(12) United States Patent
Kelly

(10) Patent No.: US 9,075,059 B2
(45) Date of Patent: Jul. 7, 2015

(54) COMPOSITIONS AND METHODS FOR DETECTING PLECTIN-1 AS A BIOMARKER FOR CANCER

(75) Inventor: Kimberly A. Kelly, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 50 days.

(21) Appl. No.: 13/508,120

(22) PCT Filed: Nov. 5, 2010

(86) PCT No.: PCT/US2010/055632
§ 371 (c)(1),
(2), (4) Date: May 4, 2012

(87) PCT Pub. No.: WO2011/057078
PCT Pub. Date: May 12, 2011

(65) Prior Publication Data
US 2012/0219499 A1     Aug. 30, 2012

Related U.S. Application Data

(60) Provisional application No. 61/258,242, filed on Nov. 5, 2009.

(51) Int. Cl.
| | |
|---|---|
| *A61K 51/08* | (2006.01) |
| *G01N 21/64* | (2006.01) |
| *A61K 49/00* | (2006.01) |
| *G01N 24/10* | (2006.01) |
| *G01N 29/00* | (2006.01) |
| *C07K 19/00* | (2006.01) |
| *G01N 33/574* | (2006.01) |
| *G01N 21/76* | (2006.01) |
| *C07K 14/00* | (2006.01) |
| *A61K 47/48* | (2006.01) |
| *C07K 7/06* | (2006.01) |
| *G01N 33/531* | (2006.01) |

(52) U.S. Cl.
CPC ............. *G01N 33/574* (2013.01); *C07K 14/00* (2013.01); *A61K 47/48246* (2013.01); *A61K 49/0002* (2013.01); *A61K 51/088* (2013.01); *C07K 7/06* (2013.01); *G01N 33/531* (2013.01); *G01N 2333/4724* (2013.01)

(58) Field of Classification Search
CPC ............ A61K 38/00; A61K 47/48246; A61K 49/0002; A61K 49/0032; A61K 49/0056; A61K 49/1818; A61K 51/088; C07K 7/06; G01N 33/531; G01N 33/533; G01N 33/57438; G01N 2333/4724; G01N 33/574
USPC .......................................................... 530/300
See application file for complete search history.

(56) References Cited

U.S. PATENT DOCUMENTS

| | | | |
|---|---|---|---|
| 7,261,876 | B2 | 8/2007 | Arbogast et al. |
| 7,563,433 | B2 | 7/2009 | McBride et al. |
| 7,666,979 | B2 | 2/2010 | Fan et al. |
| 8,044,175 | B2 | 10/2011 | Dransfield et al. |
| 2005/0214859 | A1 | 9/2005 | Dransfield et al. |
| 2008/0108795 | A1 | 5/2008 | Guo et al. |
| 2008/0267882 | A1 | 10/2008 | Chen et al. |
| 2010/0189689 | A1 | 7/2010 | Chang et al. |

FOREIGN PATENT DOCUMENTS

| | | |
|---|---|---|
| CN | 1297902 A | 6/2001 |
| CN | 1905894 A | 1/2007 |
| CN | 102762984 A | 10/2012 |
| EP | 2496948 A2 | 9/2012 |
| WO | WO-2009097579 A1 | 8/2009 |
| WO | WO2009129220 * | 10/2009 |
| WO | WO-2009132020 A2 | 10/2009 |
| WO | WO-2011057078 A3 | 5/2011 |

OTHER PUBLICATIONS

Sosabowski et al. (Nature Protocols, vol. 1 No. 2, 2006).*
Veronese et al. (Biomaterials 22 (2001) 405-417.*
"Chinese Application Serial No. 201080060246.8, Office Action mailed Feb. 20, 2014", 11 pgs.
"European Application Serial No. 08827534.2, Response filed Jan. 7, 2013 to Office Action mailed Jun. 28, 2012", 14 pgs.
"European Application Serial No. 10829151.9, Extended European Search Report mailed Apr. 7, 2014", 7 pgs.
"European Application Serial No. 10829151.9, Office Action mailed Jun. 28, 2012", 2 pgs.
"International Application Serial No. PCT/US2010/055632, International Preliminary Report on Patentability mailed May 18, 2012", 7 pgs.
"International Application Serial No. PCT/US2010/055632, International Search Report mailed Jul. 28, 2011", 5 pgs.
"International Application Serial No. PCT/US2010/055632, Written Opinion mailed Jul. 28, 2011", 5 pgs.
Bausch, D., et al., "Plectin-1 is a biomarker of malignant pancreatic intraductal papillary mucinous neoplasms", J Gastrointest Surg., 13(11), (Nov. 2009), 1948-54.
Burrows, S. R, et al., "Peptide-MHC class I tetrameric complexes display exquisite ligand specificity", J Immunol., 165(11), (Dec. 1, 2000), 6229-34.
Chakraborty, S., et al., "Evaluation of 111In-labeled cyclic RGD peptides: tetrameric not tetravalent", Bioconjug Chem., 21(5), (May 19, 2010), 969-78.
Chen, X., et al., "MicroPET and autoradiographic imaging of breast cancer alpha v-integrin expression using 18F- and 64Cu-labeled RGD peptide", Bioconjug Chem., 15(1), (Jan.-Feb. 2004), 41-9.

(Continued)

*Primary Examiner* — Louise Humphrey
*Assistant Examiner* — Tara Martinez
(74) *Attorney, Agent, or Firm* — Rodney L. Sparks

(57) ABSTRACT

The present invention provides compositions and methods useful for diagnostic and imaging techniques for detecting and localizing the biomarker Plectin-1. The present invention provides multimeric peptide ligand complexes for targeting Plectin-1, such as the multimeric peptide ligand complex having the formula (βAKTLLPTPGGS(PEG5000))4 KKKKDOTAβA-NH$_2$, to which imaging agents and/or therapeutic agents can be conjugated.

19 Claims, 13 Drawing Sheets

(56) References Cited

OTHER PUBLICATIONS

Chen, X., et al., "MicroPET imaging of breast cancer alphav-integrin expression with 64Cu-labeled dimeric RGD peptides", Mol Imaging Biol., 6(5), (Sep.-Oct. 2004), 350-9.

Chen, X., et al., "Pharmacokinetics and tumor retention of 125I-labeled RGD peptide are improved by PEGylation", Nucl Med Biol., 31(1), (Jan. 2004), 11-9.

Choe, Y. S, et al., "Targeted in vivo imaging of angiogenesis: present status and perspectives", Curr Pharm Des., 13(1), (2007), 17-31.

Dijkgraaf, I., et al., "PET imaging of αvβ3 integrin expression in tumours with 68Ga-labelled mono-, di- and tetrameric RGD peptides", Eur J Nucl Med Mol Imaging., 38(1), Epub Sep. 21, 2010 (Jan. 2011), 128-37.

Harris, T. J, et al., "Evaluation of plectin-1 immunohistochemical staining in human non-small cell lung cancer", Journal of Clinical Oncology, ASCO Annual Meeting Proceedings (Post-Meeting Edition), Vol , No. 15S ( Supplement), (2009), e22118.

Janssen, M., et al., "Comparison of a monomeric and dimeric radiolabeled RGD-peptide for tumor targeting", Cancer Biother Radiopharm., 17(6), (Dec. 2002), 641-6.

Kelly, Kimberly A, et al., "Targeted nanoparticles for imaging incipient pancreatic ductal adenocarcinoma", PLoS Med., 5(4): e85, (Apr. 15, 2008), 0657-0668.

Krajewski, K., et al., "Effect of Dimerization and Tetramerization on the Potency of HIV-1 Integrase Inhibitory Peptides", Understanding Biology Using Peptides, American Peptide Symposia, vol. 9, (2006), 411-412.

Lee, K. Y, et al., "An early evaluation of malignant tendency with plectin expression in human colorectal adenoma and adenocarcinoma", J Med., 35(1-6), (2004), 141-9.

Leung, Kam, "Lys-Thr-Leu-Leu-Pro-Thr-Pro-cross-linked iron oxide-Cy5.5", Molecular Imaging and Contrast Agent Database(MICAD), (Aug. 8, 2008), 4 pgs.

Li, S., et al., "Synthesis and characterization of a high-affinity {alpha}v{beta}6-specific ligand for in vitro and in vivo applications", Mol Cancer Ther., 8(5), (May 2009), 1239-49.

Li, Z. B, et al., "(64)Cu-labeled tetrameric and octameric RGD peptides for small-animal PET of tumor alpha(v)beta(3) integrin expression", J Nucl Med., 48(7), (Jul. 2007), 1162-71.

Nahrendorf, M., et al., "18F-4V for PET-CT imaging of VCAM-1 expression in atherosclerosis", JACC Cardiovasc Imaging, 2(10), (Oct. 2009), 1213-22.

Niwa, T., et al., "BRCA2 interacts with the cytoskeletal linker protein plectin to form a complex controlling centrosome localization", Cancer Sci., 100(11), (Nov. 2009), 2115-25.

Pfendner, E., et al., "Plectin gene mutations can cause epidermolysis bullosa with pyloric atresia.", J Invest Dermatol., 124(1), (Jan. 2005), 111-5.

Poethko, T., et al., "Two-step methodology for high-yield routine radiohalogenation of peptides: (18)F-labeled RGD and octreotide analogs", J Nucl Med., 45(5), (May 2004), 892-902.

Ponticelli, S., et al., "Modulation of angiogenesis by a tetrameric tripeptide that antagonizes vascular endothelial growth factor receptor 1", J Biol Chem., 283(49), (Dec. 5, 2008), 34250-9.

Pulkkinen, L., et al., "Homozygous deletion mutations in the plectin gene (PLEC1) in patients with epidermolysis bullosa simplex associated with late-onset muscular dystrophy", Hum Mol Genet., 5(10), (Oct. 1996), 1539-46.

Sonnenberg, A., et al., "Plakins in development and disease", Exp Cell Res., 313(10), (Jun. 10, 2007), 2189-203.

Yim, C. B, et al., "Synthesis of DOTA-conjugated multimeric [Tyr3]octreotide peptides via a combination of Cu(I)-catalyzed "click" cycloaddition and thio acid/sulfonyl azide "sulfo-click" amidation and their in vivo evaluation", J Med Chem., 53(10), (May 27, 2010), 3944-53.

\* cited by examiner

SEQUENCE LISTING

```
<160> NUMBER OF SEQ ID NOS: 23

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Lys Thr Leu Leu Pro Thr Pro
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic random sequence having the modified
      amino acid beta alanine (bAla) as a residue
<220> FEATURE:
<221> NAME/KEY: MUTAGEN
<222> LOCATION: (1)..(8)
<223> OTHER INFORMATION: bAla
<220> FEATURE:
<221> NAME/KEY: MUTAGEN
<222> LOCATION: (1)..(8)
<220> FEATURE:
<221> NAME/KEY: misc_feature
<222> LOCATION: (1)..(8)
<223> OTHER INFORMATION: bAla
<220> FEATURE:
<221> NAME/KEY: misc_feature
<222> LOCATION: (1)..(8)
```

```
<223> OTHER INFORMATION: bAla
<220> FEATURE:
<221> NAME/KEY: mutagen
<222> LOCATION: (1)..(8)
<223> OTHER INFORMATION: bAla, modified from Seq Id NO:1

<400> SEQUENCE: 2

Xaa Lys Thr Leu Leu Pro Thr Pro
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic random sequence having the modified
      amino acid beta alanine (bAla) as a residue
<220> FEATURE:
<221> NAME/KEY: MUTAGEN
<222> LOCATION: (1)..(11)
<223> OTHER INFORMATION: bAla
<220> FEATURE:
<221> NAME/KEY: misc_feature
<222> LOCATION: (1)..(11)
<223> OTHER INFORMATION: bAla
<220> FEATURE:
<221> NAME/KEY: misc_feature
<222> LOCATION: (1)..(11)
<223> OTHER INFORMATION: bAla

<400> SEQUENCE: 3

Xaa Lys Thr Leu Leu Pro Thr Pro Gly Gly Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic random sequence having the modified
      amino acid beta alanine (bAla) as a residue
<220> FEATURE:
<221> NAME/KEY: MUTAGEN
<222> LOCATION: (1)..(10)

<400> SEQUENCE: 4

Lys Thr Thr Leu Pro Thr Pro Gly Gly Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic randomly generated sequence

<400> SEQUENCE: 5

Lys His Val Met Ser Lys Gln
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic randomly generated sequence

<400> SEQUENCE: 6

Lys His Val Met Ser Lys Gln Gly Gly Ser
1               5                   10
```

```
<210> SEQ ID NO 7
<211> LENGTH: 8
<212> TYPE: PRT
<213> ORGANISM: Artificial Sequence
<220> FEATURE:
<223> OTHER INFORMATION: Synthetic randomly generating sequence
      containing the modified amino acid beta alanine (bAla) as a
      residue
<220> FEATURE:
<221> NAME/KEY: MUTAGEN
<222> LOCATION: (1)..(8)
<223> OTHER INFORMATION: bAla

<400> SEQUENCE: 7

Xaa Lys His Val Met Ser Lys Gln
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic randomly generating sequence
      containing the modified amino acid beta alanine (bAla) as a
      residue
<220> FEATURE:
<221> NAME/KEY: MUTAGEN
<222> LOCATION: (1)..(11)
<223> OTHER INFORMATION: bAla

<400> SEQUENCE: 8

Xaa Lys His Val Met Ser Lys Gln Gly Gly Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic randomly genertated sequence
<220> FEATURE:
<221> NAME/KEY: MUTAGEN
<222> LOCATION: (1)..(7)

<400> SEQUENCE: 9

Ala Thr Leu Leu Pro Thr Pro
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic randomly generated sequence
<220> FEATURE:
<221> NAME/KEY: MUTAGEN
<222> LOCATION: (1)..(7)

<400> SEQUENCE: 10

Lys Ala Leu Leu Pro Thr Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic randomly generated sequence
<220> FEATURE:
```

```
<221> NAME/KEY: MUTAGEN
<222> LOCATION: (1)..(7)

<400> SEQUENCE: 11

Lys Thr Ala Leu Pro Thr Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic randomly generated sequence
<220> FEATURE:
<221> NAME/KEY: MUTAGEN
<222> LOCATION: (1)..(7)

<400> SEQUENCE: 12

Lys Thr Leu Ala Pro Thr Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic randomly generated sequence
<220> FEATURE:
<221> NAME/KEY: MUTAGEN
<222> LOCATION: (1)..(7)

<400> SEQUENCE: 13

Lys Thr Leu Leu Ala Thr Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic randomly generated sequence
<220> FEATURE:
<221> NAME/KEY: MUTAGEN
<222> LOCATION: (1)..(7)

<400> SEQUENCE: 14

Lys Thr Leu Leu Pro Ala Pro
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic randomly generated sequence
<220> FEATURE:
<221> NAME/KEY: MUTAGEN
<222> LOCATION: (1)..(7)

<400> SEQUENCE: 15

Lys Thr Thr Leu Pro Thr Ala
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic randomly generating sequence
``` containing the modified amino acid beta alanine (bAla) as a
      residue
<220> FEATURE:
<221> NAME/KEY: MUTAGEN
<222> LOCATION: (1)..(11)
<223> OTHER INFORMATION: bAla

<400> SEQUENCE: 16

Xaa Ala Thr Leu Leu Pro Thr Pro Gly Gly Ser
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic randomly generating sequence
      containing the modified amino acid beta alanine (bAla) as a
      residue
<220> FEATURE:
<221> NAME/KEY: MUTAGEN
<222> LOCATION: (1)..(11)
<223> OTHER INFORMATION: bAla

<400> SEQUENCE: 17

Xaa Lys Ala Leu Leu Pro Thr Pro Gly Gly Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic randomly generating sequence
      containing the modified amino acid beta alanine (bAla) as a
      residue
<220> FEATURE:
<221> NAME/KEY: MUTAGEN
<222> LOCATION: (1)..(11)
<223> OTHER INFORMATION: bAla

<400> SEQUENCE: 18

Xaa Lys Thr Ala Leu Pro Thr Pro Gly Gly Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic randomly generating sequence
      containing the modified amino acid beta alanine (bAla) as a
      residue
<220> FEATURE:
<221> NAME/KEY: MUTAGEN
<222> LOCATION: (1)..(11)
<223> OTHER INFORMATION: bAla

<400> SEQUENCE: 19

Xaa Lys Thr Leu Ala Pro Thr Pro Gly Gly Ser
1               5                   10

```
<210> SEQ ID NO 20
<211> LENGTH: 11
<212> TYPE: PRT
<213> ORGANISM: Artificial Sequence
<220> FEATURE:
<223> OTHER INFORMATION: Synthetic randomly generating sequence
      containing the modified amino acid beta alanine (bAla) as a
      residue
<220> FEATURE:
<221> NAME/KEY: MUTAGEN
<222> LOCATION: (1)..(11)
<223> OTHER INFORMATION: bALA

<400> SEQUENCE: 20

Xaa Lys Thr Leu Leu Ala Thr Pro Gly Gly Ser
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic randomly generating sequence
      containing the modified amino acid beta alanine (bAla) as a
      residue
<220> FEATURE:
<221> NAME/KEY: MUTAGEN
<222> LOCATION: (1)..(11)
<223> OTHER INFORMATION: bAla

<400> SEQUENCE: 21

Xaa Lys Thr Leu Leu Pro Ala Pro Gly Gly Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic randomly generating sequence
      containing the modified amino acid beta alanine (bAla) as a
      residue
<220> FEATURE:
<221> NAME/KEY: MUTAGEN
<222> LOCATION: (1)..(11)
<223> OTHER INFORMATION: bAla

<400> SEQUENCE: 22

Xaa Lys Thr Leu Leu Pro Thr Ala Gly Gly Ser
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Synthetic randomly generated sequence

<400> SEQUENCE: 23

Lys Lys Lys Lys
1
```

COMPOSITIONS AND METHODS FOR DETECTING PLECTIN-1 AS A BIOMARKER FOR CANCER

CROSS REFERENCE TO RELATED APPLICATIONS

This application is entitled to priority pursuant to 35 U.S.C. §119(e) to U.S. provisional patent application No. 61/258,242, filed on Nov. 5, 2009.

STATEMENT REGARDING FEDERALLY SPONSORED RESEARCH OR DEVELOPMENT

This invention was made with United States Government support under Grant Nos. NIH-P50-CA86355 and PO1-CA117969-01, awarded by The National Institutes of Health. The United States Government has certain rights in the invention.

BACKGROUND

Pancreatic cancer (PDAC) is the 4th leading cause of cancer-related death in the U.S. and other industrialized countries [1]. Despite massive efforts, it remains a devastating disease, its 5 year survival rate is less than 5% and average median survival is less than 1 year [1]. This grim prognosis is mostly due to its often late initial diagnosis at an incurable advanced stage, frequently after metastasis.

PDAC is believed to progress through precursor lesions termed pancreatic intraepithelial neoplasia (PanIN) to invasive cancer, similar to the adenoma-carcinoma sequence observed in other malignancies. Lesions progress from adenoma (PanIN I) to adenoma with dysplasia (PanIN II), to carcinoma in situ (PanIN III) and finally invasive cancer [2, 3, 4]. Despite this well characterized carcinogenesis through precursor lesions, effective early detection and screening for PDAC are still unavailable. This is mostly due to the absence of diagnostic tools and biomarkers for early cancer. Ideally, a biomarker for PDAC should therefore not only detect invasive cancer, but also its precursor lesions, PanIN II and more importantly pre-invasive malignant PanIN III lesions. Currently, CA 19.9 is the only clinically used serum biomarker for PDAC. However, it lacks specificity and sensitivity, especially for the detection of small cancers and the differentiation of malignant and benign pancreatic disease [5]. CA 19.9 is therefore unsuitable for screening or early detection of PDAC. Invasive endoscopic procedures (EUS and ERCP) can detect some early lesions, but suffer from potential for injury to the pancreas, high false negative rates and are highly operator dependent [6, 7]. They also often fail to distinguish malignant from benign or premalignant lesions [8, 9]. Cross-sectional abdominal imaging has also proven unreliable for the detection of early stage PDAC, especially in high-risk patients [10, 11]. It fails to detect metastases in up to 30% of patients with PDAC preoperatively [12, 13] and does not safely differentiate between chronic pancreatitis (CP) and PDAC [14, 15]. The reliable distinction of PDAC and chronic pancreatitis is important, but often difficult to make. Both diseases share many clinical signs and symptoms, but profoundly different treatment strategies are employed for each. While the only available curative treatment for PDAC is radical surgical resection, the treatment of chronic pancreatitis is focused on symptomatic improvement, which most often can be achieved without surgery [14, 15].

Novel biomarkers and non-invasive imaging strategies that overcome the shortcomings of currently employed diagnostic tools, would allow a reliable distinction of PDAC and chronic pancreatitis. They would also permit the earlier diagnosis and consequently treatment of PDAC before the onset of metastasis. They are therefore much needed and may ultimately aid in improving survival [16]. Recently, Plectin-1 (Plec1) was suggested to be a potential novel imaging biomarker for PDAC based on findings in vitro and in a genetically engineered mouse model [17]. Peptide ligands were identified for use in detecting Plec1 [17]. However, the suitability of Plec1 as a biomarker for human PDAC and its precursor lesions remains to be assessed. Plec1 has been identified as a biomarker for malignant pancreatic "intraductal papillary mucinous neoplasms" (IPMN) and has been hypothesized to be a marker for the early detection of carcinoma arising in IPMN (Bausch et al., 2009, J. Gastrointest. Surg., 13:1948), as a biomarker for non-small cell lung cancer (Harris, 2009, J. Clin. Oncology, 27, No. 15S (May 20 Supplement): e22118), and for human colorectal adenoma and adenocarcinoma (Lee, 2004, J. Med., 35:(1-6):141-149). One peptide ligand for Plec1 is the peptide KTLLPTP (SEQ ID NO:1) [Kelly et al. (2008) Targeted nanoparticles for imaging incipient pancreatic ductal adenocarcinoma. PLoS Med 5:4:e85; International Pat. Pub. No. WO 2009/129220, Kelly et al., published Oct. 22, 2009].

There is a long felt need in the art for better cancer biomarkers, for new and better reagents which recognize biomarkers, to aid in diagnosing, monitoring, and localizing cancers. The present invention satisfies these needs.

SUMMARY OF THE INVENTION

The present invention is based on a novel branched multimeric peptide imaging complex described herein which targets Plectin-1, and also on the surprising results obtained with the complex.

Plectin-1 (GenBank accession number AAR95677) is specifically upregulated in early preinvasive, primary and metastatic human PDAC. In a preclinical model, Plectin-1 is one of the first biomarkers for PDAC that can be used for non-invasive imaging. Taken together, these data suggest that Plec1 is a sensitive and specific biomarker for PDAC and may be utilized to improve its detection and staging.

The present invention provides a multimeric peptide ligand complex for binding to Plectin-1 or a homolog or fragment thereof, said complex comprising at least two peptides that independently bind to Plectin-1 or a homolog or fragment thereof. In one aspect, each of the peptides that bind to Plectin-1 or a homolog or fragment thereof, independently and optionally comprise at least one non-standard amino acid substitution or conservative amino acid substitution or addition. In one aspect, each of the peptides of the multimer, independently, is optionally modified by adding at least one additional amino acid. In one aspect, each of the peptides of the multimer is independently and optionally coupled to polyethylene glycol. In one aspect, each of the peptides of the multimer or peptides optionally coupled to polyethylene glycol is further coupled to a chelating agent. Optionally the chelating agent is coupled by at least one linker to the peptides or peptides optionally coupled to polyethylene glycol. Optionally, at least one imaging agent is coupled to said chelating agent and optionally at least one therapeutic agent is coupled to said chelating agent.

In one aspect, the multimer is selected from the group consisting of a dimer, a trimer, a tetramer, pentamer, hexamer, heptamer, and octamer.

In one aspect, the multimeric peptide ligand complex is a homomultimer or a heteromultimer. In one aspect, the homomultimer is a tetramer.

In one embodiment, the multimeric peptide ligand complex comprises a chelator selected from the group consisting of DTPA, DO3A, DOTA, EDTA, TETA, EHPG, HBED, NOTA, DOTMA, TETMA, PDTA, TTHA, LICAM, HYNIC, and MECAM.

In one aspect, the polyethylene glycol is polyethylene glycol 5000.

In one embodiment, the multimeric peptide ligand complex comprises an imaging agent selected from the group consisting of a radionuclide, a radiological contrast agent, a paramagnetic ion, a metal, a biological tag, a fluorescent label, a chemiluminescent label, an ultrasound contrast agent and a photoactive agent. In one aspect, the imaging agent is a radionuclide. In one aspect, the radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, and other gamma-, beta-, or positron-emitters. In one aspect, the radionuclide is $^{111}$In.

In one aspect, the multimeric peptide ligand complex comprises peptides which independently have a sequence selected from the group consisting of SEQ ID NOs:1-4 and 9-22. In one aspect, the sequences are selected from the group consisting of SEQ ID NOs:1-4. SEQ ID NO:1 (KTLLPTP) is the base peptide ligand, and the other sequences are modifications of it (see Examples and FIG. 9):

```
SEQ ID NO: 2-    βAKTLLPTP

SEQ ID NO: 3-    βAKTLLPTPGGS

SEQ ID NO: 4-    KTLLPTPGGS

SEQ ID NO: 9-    ATLLPTP

SEQ ID NO: 10-   KALLPTP

SEQ ID NO: 11-   KTALPTP

SEQ ID NO: 12-   KTLAPTP

SEQ ID NO: 13-   KTLLATP

SEQ ID NO: 14-   KTLLPAP

SEQ ID NO: 15-   KTLLPTA

SEQ ID NO: 16-   βAATLLPTPGGS

SEQ ID NO: 17-   βAKALLPTPGGS

SEQ ID NO: 18-   βAKTALPTPGGS

SEQ ID NO: 19-   βAKTLAPTPGGS

SEQ ID NO: 20-   βAKTLLATPGGS

SEQ ID NO: 21-   βAKTLLPAPGGS

SEQ ID NO: 22-   βAKTLLPTAGGS    (SEQ ID NO: 22)
```

Note that the beta alanine residues are provided as Xaa in the Sequence Listing provided herewith. The sequences can be modified, including amino acid substitutions and additions which do not substantially effect binding of these peptides to Plectin-1 or homologs or fragments thereof. Although alanine substitutions are demonstrated above, substitutions using other amino acids are encompassed by the invention. Additionally, the data disclosed herein suggest the importance of threonine in the sequence, and also proline.

Peptides of the invention are useful as multimers. Additionally, the multimers can be modified by the addition of amino acids such as beta alanine (βA) and polyethylene glycol to increase stability, half-life in the blood stream and tissues, decrease degradation, etc. One of ordinary skill in the art will appreciate that the orientation of the sequences in the complex can in some cases be changed and that the multimer can be a heteromultimer or a homomultimer.

In one embodiment, the multimeric complex is a tetramer and has the formula (βAKTLLPTPGGS(PEG5000))$_4$ KKKKDOTAβA-NH$_2$, which is depicted by its chemical structure in FIG. 8. FIG. 8 further indicates an imaging agent coupled to DOTA. In one aspect, the tetrameric complex has a Ki of about $8.3\times10^{-7}$ M. In one embodiment, the imaging agent is $^{111}$In. In one aspect, the imaging agent is detected with a SPECT/CT scanner coupled to a computer, and analyzing imaging data using a program.

The invention further provides a method for detecting Plectin-1 or a homolog or fragment thereof in a subject. The method comprises administering to a subject a multimeric peptide ligand complex comprising an imaging agent, and detecting the location of cells comprising Plectin-1.

In one aspect, the method comprises the use of peptide ligands in the multimer peptide ligand imaging complex wherein each peptide ligand has a sequence independently selected from the group consisting of SEQ ID NOs:1-4 and 9-22.

In one aspect, the method provides for the use of an imaging agent selected from the group consisting of a radionuclide, a radiological contrast agent, a paramagnetic ion, a metal, a biological tag, a fluorescent label, a chemiluminescent label, an ultrasound contrast agent and a photoactive agent. One of ordinary skill in the art will understand that the method of detection used will depend on the particular imaging agent used.

In one aspect of the method, Plectin-1 or a homolog or fragment thereof is a cell surface Plectin-1 or a homolog or fragment thereof.

The invention further provides a method for detecting cancer, diagnosing cancer, monitoring the progression of cancer, or monitoring treatment of a cancer, wherein the cancer cells express or present Plectin-1 or a homolog or fragment thereof. The method comprises administering to a test subject a pharmaceutical composition comprising a multimeric peptide ligand complex wherein the complex comprises an imaging agent, and then detecting the imaging agent and determining the levels and location of the imaging agent in a test subject. A comparison of the levels and location in the test subject is made with the levels and location of the imaging agent from an otherwise identical location from an unaffected subject or with an unaffected area of the test subject. A higher level or different location of the imaging agent in the test subject compared with the level or location of the imaging agent in said sample from an unaffected subject or from an unaffected area of the test subject, is an indication that the test subject has a cancer expressing or presenting Plectin-1 or a homolog or fragment thereof. The levels or location of the detected imaging agent is an indicator of the location and amount of the biomarker Plectin-1.

In one embodiment, the cancer is selected from the group consisting of head and neck cancer, liver cancer, pancreatic cancer, esophageal cancer, stomach cancer, lung cancer, breast cancer, ovarian cancer, uterine cancer, endometrial cancer, cervical cancer, prostate cancer, adrenal cancer, lymphoma, salivary gland cancer, bone cancer, brain cancer, cerebellar cancer, colon cancer, rectal cancer, colorectal cancer, oronasopharyngeal cancer, NPC, kidney cancer, bladder cancer, skin cancer, melanoma, basal cell carcinoma, hard palate carcinoma, squamous cell carcinoma of the tongue, meningioma, pleomorphic adenoma, astrocytoma, chondrosarcoma, cortical adenoma, hepatocellular carcinoma, pancreatic cancer, squamous cell carcinoma, and adenocarcinoma.

In one aspect, the cancer is pancreatic cancer. In one aspect, the pancreatic cancer is selected from the group consisting of pancreatic ductal adenocarcinoma, pancreatic intraepithelial neoplasia, adenoma, adenoma with dysplasia, and carcinoma in situ.

In one embodiment, the cancer is a metastatic cancer.

The invention is also useful for comparing the levels of Plectin-1 being imaged to help determine whether a cancer is benign or malignant, based on the level of imaging agent detected (a measure of the amount of Plectin-1).

The invention is also useful for determining the stage of carcinogenesis of a cancer and monitoring its progression from early to late stage cancer. This method is useful for determining the type and amount of therapy to use.

In one embodiment of the method of the invention, the peptides of the multimeric peptide ligand complex each have a sequence independently selected from the group consisting of SEQ ID NOs:1-4 and 9-22.

In one embodiment of the method of the invention the multimeric peptide ligand complex has the formula (βAKTLLPTPGGS(PEG5000))$_4$ KKKKDOTAβA-NH$_2$ and the imaging agent is $^{111}$In.

In one embodiment of the method, the imaging agent is selected from the group consisting of a radionuclide, a radiological contrast agent, a paramagnetic ion, a metal, a biological tag, a fluorescent label, a chemiluminescent label, an ultrasound contrast agent and a photoactive agent.

In one embodiment of the invention, Plectin-1 or a homolog or fragment thereof is a cell surface Plectin-1 or a homolog or fragment thereof.

The invention further provides compositions and methods for diagnosing cancer in a subject, wherein cells of the cancer express Plectin-1 or a homolog or fragment thereof. The method comprises obtaining a biological sample from the subject, contacting the sample with a composition comprising a multimeric peptide ligand complex of claim 1, wherein the complex comprises an imaging agent. The method further provides for comparing the level or location of Plectin-1 in the sample from the test subject with the level or location of Plectin-1 from an otherwise identical sample obtained from an unaffected subject or with a standard sample comprising a known amount of Plectin-1, wherein a higher level of Plectin-1 in said sample from said test subject is an indication that said test subject has cancer.

In one embodiment of the method the multimeric peptide ligand complex has the formula (βAKTLLPTPGGS (PEG5000))$_4$ KKKKDOTAβA-NH$_2$. In one aspect, the imaging agent is selected from the group consisting of a radionuclide, a radiological contrast agent, a paramagnetic ion, a metal, a biological tag, a fluorescent label, a chemiluminescent label, an ultrasound contrast agent and a photoactive agent.

In one embodiment, the invention provides a pharmaceutical composition comprising a pharmaceutically-acceptable carrier and a multimeric peptide ligand complex which binds with Plectin-1.

The invention further encompasses a kit comprising a pharmaceutical composition comprising a pharmaceutically-acceptable carrier and a multimeric peptide ligand complex of claim 1, an applicator, and an instructional material for the use thereof, and optionally an imaging agent and a therapeutic agent.

To assess the utility of plectin-1 targeted peptides (PTP) for in vivo imaging, the present invention discloses that, in one example, peptides were synthesized in a GMP grade facility as a tetrameric structure with DOTA as a chelator for an imaging agent. In one aspect, the imaging agent is $^{111}$In. In one aspect, the peptide ligand for Plectin-1 used in the present application is the peptide KTLLPTP (SEQ ID NO:1) (Kelly et al., 2008, PLoS Medicine, 5:4:0657-0668; International Pat. Pub. No. WO 2009/129220, Kelly et al., published Oct. 22, 2009). In one aspect, the peptide ligand can be modified as described herein before preparing the multimeric peptide ligand imaging complex. In one aspect, the modified peptide ligand is In one aspect, the novel tetrameric peptide imaging complex of the invention has the formula: (βAKTLLPT-PGGS(PEG5000))$_4$KKKKDOTAβA-NH$_2$ (also referred to as [(βAla-Lys-Thr-Leu-Leu-Pro-Thr-Pro-Gly-Gly-Ser-PEG5K)$_2$-Lys]$_2$-Lys-Lys(DOTA)-βAla-NH$_2$ herein) that is, it is a complex comprising four peptides which are ligands for Plectin-1. In one aspect, this complex further comprises an imaging agent to help visualize the location of Plectin-1 expressing cells. In one aspect, the imaging agent is $^{111}$IN.

Optionally, a therapeutic agent can be attached or can be included in a pharmaceutical composition comprising the imaging complex.

One of ordinary skill in the art will appreciate that the base peptide ligand, i.e., SEQ ID NO:1, can be oriented in the opposite direction in the complex.

In one aspect, other peptide ligands for Plectin-1 include, but are not limited to, SEQ ID NOs:1-4 and 9-22, and functional homologs, derivatives, and fragments thereof.

In one aspect, a tetrameric complex of the invention has a Ki (inhibition dissociation constant) of about 8.3×10$^{-7}$ M. In one aspect, it has a blood half-life of about 4.29 minutes when administered to a subject.

The invention further provides additional active tetrameric complexes. For example, the invention includes a complex comprising a modified SEQ ID NO:1 with three additional amino acids (Gly, Gly, and Ser), that is KTLLPTPGGS (SEQ ID NO:4). The tetrameric complex has the formula [Lys-Thr-Leu-Leu-Pro-Thr-Pro-Gly-Gly-Ser]$_4$-Lys$_4$-βAla-DOTA, also referred to as [KTLLPTPGGS]$_4$-K$_4$-βA-DOTA, with the structure of FIG. 7.

Lysine (K) has the structure:

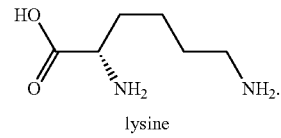

lysine

Clinically relevant SPECT tracers as used herein enable the detection of small PDAC and metastases.

In one aspect, the imaging agent or detectable moiety includes, but is not limited to, a radionuclide, a radiological contrast agent, a paramagnetic ion, a metal, a biological tag, a fluorescent label, a chemiluminescent label, an ultrasound contrast agent and a photoactive agent.

The tetrameric peptide imaging complexes of the invention are surprisingly more sensitive than previously known agents. Additionally, the tetrameric peptide imaging complexes of the invention work surprisingly more quickly that known agents.

The present application further discloses the expression of Plectin-1 in many types of cancer (FIG. 2). Therefore, the present invention encompasses the use of the multimeric peptide imaging complexes of the invention for detecting, diagnosing, and localizing cancers other than pancreatic cancers.

The present invention further provides for quantifying levels of Plectin-1, and thus encompasses the ability to distinguish normal, benign, and malignant tissue. In one aspect, the multimer peptide imaging complexes comprise tetrameric peptides.

The present invention further provides kits comprising at least one multimeric peptide ligand complex of the invention, an instructional material, and optionally includes at least one imaging agent and optionally at least one therapeutic agent.

Various aspects and embodiments of the invention are described in further detail below.

DETAILED DESCRIPTION

Abbreviations and Acronyms

Figure 1A:
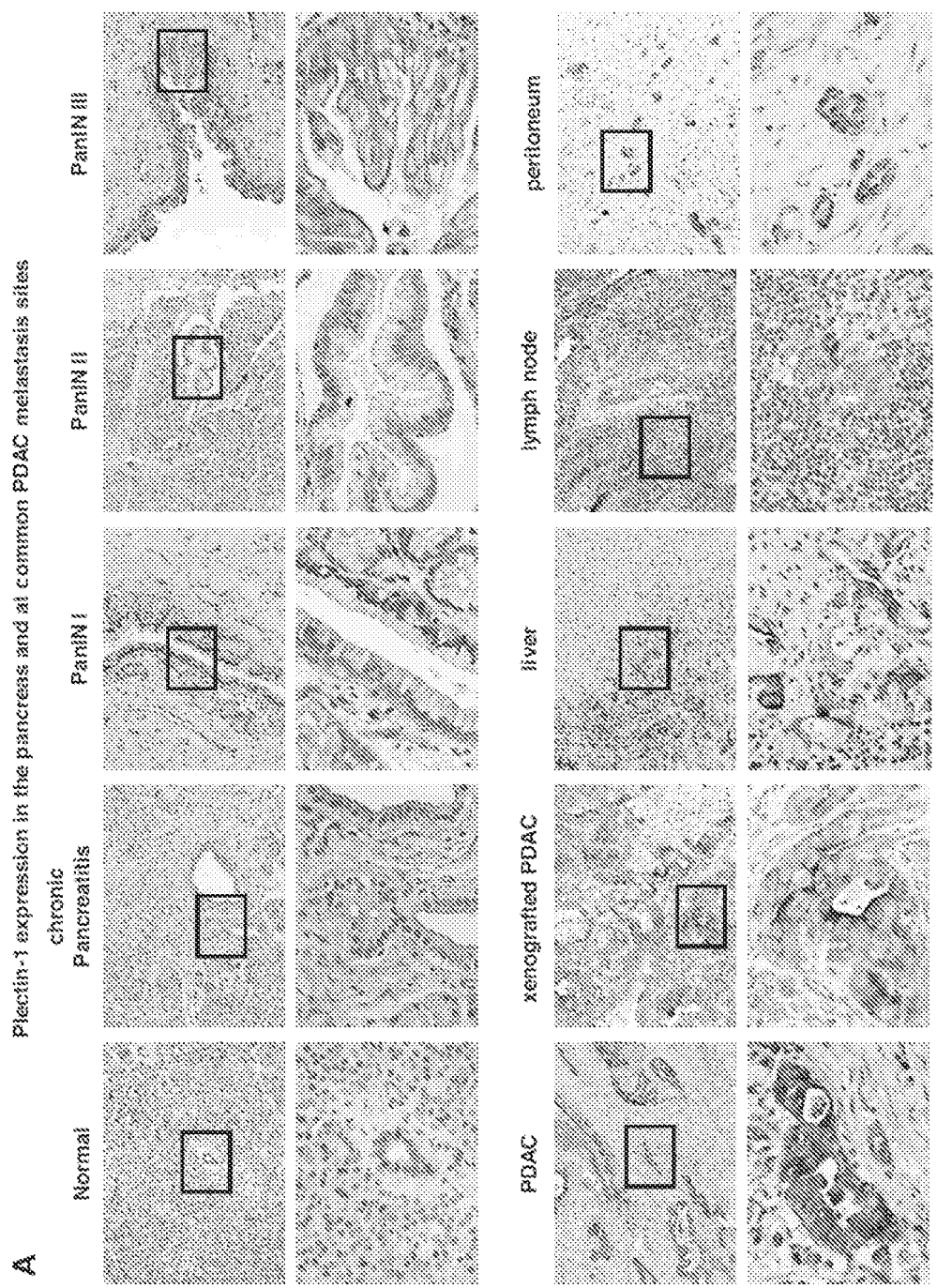
FIG. 1: Plectin-1 Immunohistochemistry and Western Blot. A) Representative images of the evaluated normal pancreata, chronic Pancreatitis, PanIN, PDAC, xenografted PDAC and PDAC metastasis sites (liver, lymph node and peritoneum). Overview (upper panel) and detailed view of the black box (lower panel). Chronic pancreatitis weakly stains for Plectin-1, while normal pancreas does not express Plectin-1. PanINs demonstrate a weak to moderate membranous staining pattern. PDAC and PDAC xenograft tissue stain moderately to strongly cytoplasmic and membranous for Plectin-1. Common PDAC metastasis sites do not show significant Plectin-1 expression, while the tumor cells stain intensely for Plec1. B) Distribution of staining intensity in the specimens. All PDAC cases exhibited a moderate or strong staining pattern, whereas normal Pancreas and the majority of chronic Pancreatitis did not express Plectin-1. In contrast, more than half of the PanIN II lesions expressed Plec1 weakly or moderately, while the majority of PanIN III lesions were Plec1 positive. C) The cellular localization of Plec1 also changes during carcinogenesis. While it is only identified in the membrane in all PanIN I and most PanIN II lesions, it is also present in the cytoplasm in some PanIN III lesions and is always identified there in PDAC. D) Quantitative Western Blot for Plec1 from 50 mg of pancreatic tissue (snap frozen surgical specimens). No Plec1 was detected in the normal pancreas and CP, while it was present in each PDAC.
Figure 1B:
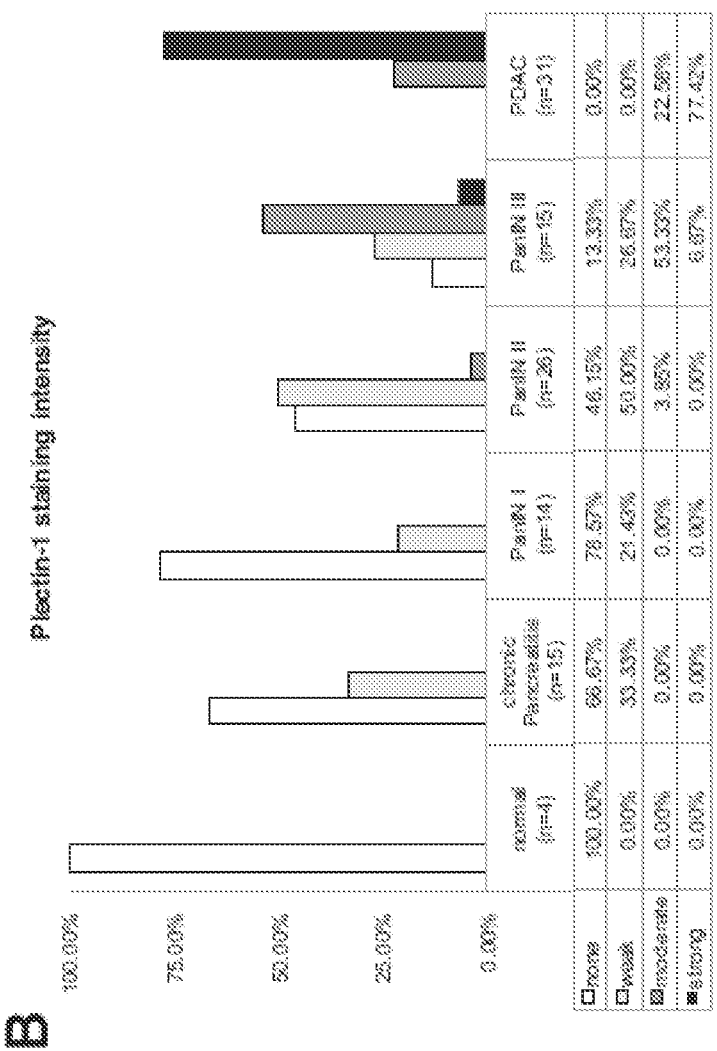
Figure 1C:
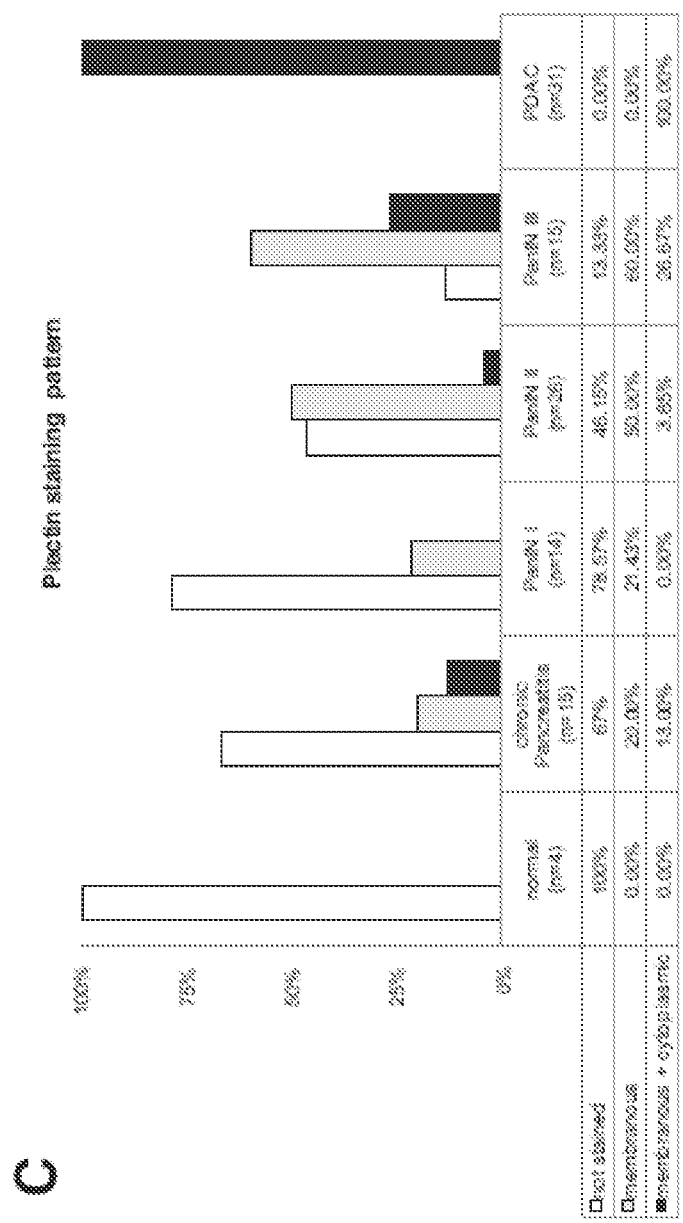
Figure 1D:
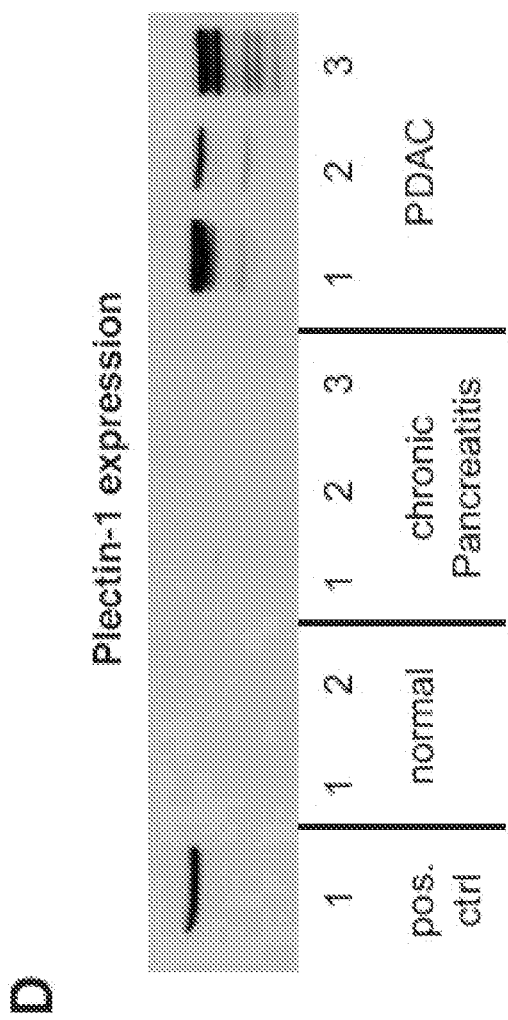

βA—beta alanine
CP—chronic pancreatitis
DOTA-1,4,7,10-tetraazacyclododecane-1,4,7,10-tetraacetic acid
ncPTP—negative control PTP
NIR—near infrared
NIRF—near infrared fluorochrome
Panc 27 peptide—KTLLPTP (SEQ ID NO:1)
PanIN—pancreatic intraepithelial neoplasia
PanIN I—adenoma PanIN II—adenoma with dysplasia
PanIN III—carcinoma in situ
PDAC—pancreatic ductal adenocarcinoma
Plec1—Plectin-1
PTP—Plectin-1 targeted peptide
SPECT—single photon emission computed tomography
tPTP—Tetrameric Plectin-1 targeted peptide, also referred to as tetrameric synthetic peptide (it targets Plectin-1)

Definitions

In describing and claiming the invention, the following terminology will be used in accordance with the definitions set forth below.

The articles "a" and "an" are used herein to refer to one or to more than one (i.e. to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

As used herein, "adenocarcinoma" refers to a cancerous tumor as opposed to an "adenoma" which refers to a benign (non-cancerous) tumor made up of cells that form glands (collections of cells surrounding an empty space).

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

The term "alterations in peptide structure" as used herein refers to changes including, but not limited to, changes in sequence, and post-translational modification.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

Amino acids have the following general structure:

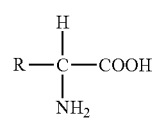

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

As used herein, the term "attach", or "attachment", or "attached", or "attaching", used herein interchangeably with "bind", or "binding" or "binds' or "bound" refers to any physical relationship between molecules that results in forming a stable complex, such as a physical relationship between a ligand, such as a peptide or small molecule, with a "binding partner" or "receptor molecule." The relationship may be mediated by physicochemical interactions including, but not limited to, a selective noncovalent association, ionic attraction, hydrogen bonding, covalent bonding, Van der Waals forces or hydrophobic attraction.

As used herein, the term "avidity" refers to a total binding strength of a ligand with a receptor molecule, such that the strength of an interaction comprises multiple independent binding interactions between partners, which can be derived from multiple low affinity interactions or a small number of high affinity interactions.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

As used herein, the term "biopsy tissue" refers to a sample of tissue that is removed from a subject for the purpose of determining if the sample contains cancerous tissue. In some embodiment, biopsy tissue is obtained because a subject is suspected of having cancer. The biopsy tissue is then examined for the presence or absence of cancer.

The term "cancer", as used herein, is defined as proliferation of cells whose unique trait—loss of normal controls—results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to a molecule of interest.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, "ductal cell", in reference to a pancreas, refers to any cell that forms or has the capability to form or originated from the ductal lining of ducts within and exiting from the pancreas.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "invasive," or "metastasis" as used herein, refers to any migration of cells, especially to invasive cancer cells or tumor cells. The term applies to normally invasive cells such as wound-healing fibroblasts and also to cells that migrate abnormally. Although the term is not to be limited by any mechanistic rationale, such cells are thought to migrate by defeating the body's means for keeping them sufficiently "in place" to function normally. Such cells are "invasive" if they migrate abnormally within a tissue or tumor, or escape the tissue, or invade other tissues.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor or target molecule.

A "receptor" or target molecule is a compound that specifically binds to a ligand.

A ligand or a receptor "specifically binds to" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

As used herein, the term "malignant" refers to having the properties of anaplasia, penetrance, such as into nearby areas or the vasculature, and metastasis.

The term "mass tag", as used herein, means a chemical modification of a molecule, or more typically two such modifications of molecules such as peptides, that can be distinguished from another modification based on molecular mass, despite chemical identity.

The term "method of identifying peptides in a sample", as used herein, refers to identifying small and large peptides, including proteins.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "pancreas" in reference to an organ refers to a collection of a plurality of cell types held together by connective tissue, such that the plurality of cells include but are not limited to acini calls, ductal cells and islet cells. The "acini" produce many of the enzymes, such as lipase, which are needed to digest food in the duodenum. The enzymes produced by the acini are carried to the duodenum by small channels called ducts. Typically, ductal cells are held in place by connective tissue in close proximity to vascular cells and nerve cells. Islets of Langerhans are typically embedded between exocrine acini units of the pancreas. Examples of islet endocrine cells are Alpha cells that secrete glucagon which counters the action of insulin while Beta cells secrete insulin, which helps control carbohydrate metabolism.

As used herein, "pancreatic cancer" refers to cancers that originate in the tissue that comprises a pancreas, such as a pancreatic ductal adenocarcinoma cell.

As used herein, "pancreatic ductal adenocarcinoma cell" refers to a cancerous cell that had the capability to form or originated from the ductal lining of the pancreas. A pancreatic ductal adenocarcinoma cell may be found within the pancreas forming a gland, or found within any organ as a metastasized cell or found within the blood stream of lymphatic system.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

As used herein, the term "peptide ligand" (or the word "ligand" in reference to a peptide) refers to a peptide or fragment of a protein that specifically binds to a molecule, such as a protein, carbohydrate, and the like. A receptor or binding partner of the peptide ligand can be essentially any type of molecule such as polypeptide, nucleic acid, carbohydrate, lipid, or any organic derived compound. Specific examples of ligands are peptide ligands of the present inventions.

The term "multimeric peptide ligand complex" refers to a complex for binding to and detecting Plectin-1 or a fragment or homolog thereof, comprising at least two peptide ligands which bind to Plectin-1. Optionally the peptide ligands are modified with conservative amino acid substitutions or additional standard or non-standards are added to enhance distribution or time before degradation, optionally additional amino acids are added as linkers, optionally moieties such as polyethylene are added to the peptide, and each of these are then attached to a chelating agent, optionally via linkers such as flexible amino acid chains, forming a multimeric peptide ligand complex. The chelating agent is useful for attachment of imaging agents. The term "multimeric peptide ligand complex" can refer to a complex with or without an imaging agent, as can the term "multimeric peptide ligand imaging complex" and the terms are meant to be used and interpreted in context. The terms can be qualified by adding the phrase with an imaging agent or the phrase without an imaging agent, or similar phrases.

The term "peptide mass labeling", as used herein, means the strategy of labeling peptides with two mass tag reagents that are chemically identical but differ by a distinguishing mass.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

As used herein, the term "post surgical tumor tissue" refers to cancerous tissue (e.g., biopsy tissue) that has been removed from a subject (e.g., during surgery).

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties. As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-$\beta$-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds, or it means that one molecule, such as a binding moiety, e.g., an oligonucleotide or antibody, binds preferentially to another molecule, such as a target molecule, e.g., a nucleic acid or a protein, in the presence of other molecules in a sample.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the peptide comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. As used herein, the term "non-cancerous" in reference to a pancreatic cell refers to a cell demonstrating regulatable cell growth and functional physiology relative to its developmental stage and activity.

As used herein, a "subject in need thereof" is a patient, animal, mammal, or human, who will benefit from the method of this invention.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO$_4$, 1 mM EDTA at 50° C. with washing in 2× standard saline citrate (SSC), 0.1% SDS at 50° C.; preferably in 7% (SDS), 0.5 M NaPO$_4$, 1 mM EDTA at 50° C. with washing in 1×SSC, 0.1% SDS at 50° C.; preferably 7% SDS, 0.5 M NaPO$_4$, 1 mM EDTA at 50° C. with washing in 0.5×SSC, 0.1% SDS at 50° C.; and more preferably in 7% SDS, 0.5 M NaPO$_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215: 3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

As used herein, the term "tumor" refers to an abnormal mass of tissue that results from excessive cell division that is uncontrolled and progressive. It is also called a neoplasm. Tumors may be either benign (not cancerous) or malignant.

As used herein, the term "tumor cell", as used herein, refers to any mass of cells that exhibits any uncontrolled growth patterns or altered physiology. Tumor cells may be derived from any tissue within an organism (e.g., a pancreatic ductal tumor cell). As used herein, the term "cancer" is a general term for more than 100 diseases that are characterized by an uncontrolled, abnormal growth of cells. Cancer cells can spread locally or can intravasate and spread via the bloodstream and lymphatic system to other parts of the body and form metastases. Cancer cells that spread are called "malignant." As used herein, the terms "cancer" and "cancerous" in reference to a physiological condition in mammals is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

By the term "vaccine," as used herein, is meant a composition which when inoculated into a subject has the effect of stimulating an immune response in the subject, which serves to fully or partially protect the subject against a condition, disease or its symptoms. In one aspect, the condition is conception. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Sequences of the Invention

```
SEQ ID NO: 1-    KTLLPTP        (SEQ ID NO: 1)
                 (also referred to as
                 Lys-Thr-Leu-Leu-Pro-Thr-Pro)

SEQ ID NO: 2-    βAKTLLPTP      (SEQ ID NO: 2)

SEQ ID NO: 3-    βAKTLLPTPGGS   (SEQ ID NO: 3)

SEQ ID NO: 4-    KTLLPTPGGS     (SEQ ID NO: 4)

SEQ ID NO: 5-    KHVMSKQ        (SEQ ID NO: 5)

SEQ ID NO: 6-    KHVMSKQGGS     (SEQ ID NO: 6)

SEQ ID NO: 7-    βAKHVMSKQ      (SEQ ID NO: 7)

SEQ ID NO: 8-    βAKHVMSKQGGS   (SEQ ID NO: 8)

SEQ ID NO: 9-    ATLLPTP        (SEQ ID NO: 9)

SEQ ID NO: 10-   KALLPTP        (SEQ ID NO: 10)

SEQ ID NO: 11-   KTALPTP        (SEQ ID NO: 11)

SEQ ID NO: 12-   KTLAPTP        (SEQ ID NO: 12)

SEQ ID NO: 13-   KTLLATP        (SEQ ID NO: 13)

SEQ ID NO: 14-   KTLLPAP        (SEQ ID NO: 14)

SEQ ID NO: 15-   KTLLPTA        (SEQ ID NO: 15)

SEQ ID NO: 16-   βAATLLPTPGGS   (SEQ ID NO: 16)

SEQ ID NO: 17-   βAKALLPTPGGS   (SEQ ID NO: 17)

SEQ ID NO: 18-   βAKTALPTPGGS   (SEQ ID NO: 18)

SEQ ID NO: 19-   βAKTLAPTPGGS   (SEQ ID NO: 19)

SEQ ID NO: 20-   βAKTLLATPGGS   (SEQ ID NO: 20)

SEQ ID NO: 21-   βAKTLLPAPGGS   (SEQ ID NO: 21)

SEQ ID NO: 22-   βAKTLLPTAGGS   (SEQ ID NO: 22)

SEQ ID NO: 23-   KKKK           (SEQ ID NO: 23)
```

βA is beta alanine, and in the sequence listing is identified as Xaa.

Embodiments

The present invention provides multimeric peptide ligand complexes useful for diagnosing, detecting, monitoring, and imaging cancer or any cell expressing Plectin-1. The peptides are used in complexes useful of imaging, diagnostics, tumor localization, etc. Methods for preparing multimeric peptides and for comparing their activity relative to the corresponding monomeric peptides, including pegylation, are described herein or can be found in the art (Li, 2007, J. Nuc. Med., 48:7:1162-1171, "$^{64}$Cu-labeled tetrameric and octameric RGD peptides for small-animal PET of tumor $α_vβ_3$ integrin expression"; reviewed in Choe and Lee, 2007, Current Pharmaceutical Design, 13:17-31; Chen et al., 2004, Mol. Imaging Biol. 6:350-9, "MicroPET imaging of breast cancer alpha$_v$-integrin expression with $^{64}$Cu-labeled dimeric RGD peptides"; Janssen, 2002, Cancer Biother. Radiopharm., 17:641-6, "Comparison of monomeric and dimeric radiolabeled RGD-peptide for tumor targeting; Poethko, 2004, J. Nucl. Med. 45:892-902; Chen, 2004, Bioconjugate Chem., 15:41-9; Chen, 2004, Nucl. Med. Biol., 31:11-19, "Pharmacokinetics and tumor retention of $^{125}$I-labeled RGD peptide are improved by PEGylation"; Li et al., 2009, Mol. Cancer. Ther., 8:5:1239-1249; U.S. Pat. No. 7,666,979 (issued from U.S. patent application Ser. No. 10/661,032); U.S. patent application Ser. No. 12/012,011 (continuation of U.S. patent application Ser. No. 10/792,582); Nahrendorf, 2010, JACC: Cardiovascular Imaging, 2:10:1213-1222; Krajewski et al., 2005, "Effect of Dimerization and Tetramerization on the Potency of HIV-Integrase Inhibitory Peptides," in Understanding Biology Using Peptides, American Peptide Society, S. Blondelle, Editor, 411-412)

Useful base peptides of the invention are described herein or in Kelly et al. (2008, Targeted nanoparticles for imaging incipient pancreatic ductal adenocarcinoma. PLoS Med 5:4: e85) and International Pat. Pub. No. WO 2009/129220 (Kelly et al., published Oct. 22, 2009) and include: SEQ ID NO:1—KTLLPTP (SEQ ID NO:1). Other useful peptides are described herein, including SEQ ID NOs:2-4 and 9-15 for binding to Plectin-1.

The invention further includes isolated nucleic acids comprising sequences encoding peptides of the invention.

In one embodiment, the useful peptides of the invention are used to prepare multimeric peptide ligand complexes and are modified by adding additional amino acids or substituting amino acids during the synthetic process. For example, the known ligand KTLLPTP (SEQ ID NO:1), which binds to Plectin-1, was used herein to form a multimeric complex and the base sequence is modified to derive the sequence βAKTLLPTPGGS (SEQ ID NO:3), to which was added a polyethylene glycol moiety, such as a PEG5000, followed by linking/spacing lysines used to connect the multiple peptides to a chelator, such as DOTA. The chelator is useful as a moiety to which an imaging agent can be added, such as $^{111}$In. The resulting multimeric peptide ligand of the invention based on these sequences, is in this case a tetramer, and has the formula (βAKTLLPTPGGS(PEG5000))$_4$KKKKDOTAβA-NH$_2$.

A chemical name for the structure having the formula (βAKTLLPTPGGS(PEG5000))$_4$KKKKDOTAβA-NH$_2$ (also referred to as [(βAla-Lys-Thr-Leu-Leu-Pro-Thr-Pro-Gly-Gly-Ser-PEG5K)$_2$-Lys]$_2$-Lys-Lys(DOTA)-βAla-NH$_2$ herein) comprising four peptide ligands (SEQ ID NO:1) of Plectin-1, as deduced by ChemDraw, is: 2,2',2"-(10-(1-(1-(2-(1-(15-amino-1'-(4-aminobutyl)-8-(1-hydroxyethyl)-2,5-di-isobutyl-4,7,10,13-tetraoxo-3,6,9,12-tetraazapentadecane) pyrrolidine-2-carboxamido)-3-hydroxybutanoyl)pyrrolidin-2-yl)-32-(1-(1-(2- (1-(15-amino-1'-(4-aminobutyl)-8-(1- hydroxyethyl)-2,5-diisobutyl-4,7,10,13-tetraoxo-3,6,9,12-tetraazapentadecane)pyrrolidine-2-carboxamido)-3-hydroxybutanoyl)pyrrolidin-2-yl)-25-(1-(1-(2-(1-(15-amino-1'-(4-aminobutyl)-8-(1-hydroxyethyl)-2,5-diisobutyl-4,7,10,13-tetraoxo-3,6,9,12-tetraazapentadecane)pyrrolidine-2-carboxamido)-3-hydroxybutanoyl)pyrrolidin-2-yl)-9-(hydroxymethyl)-1,4,7,10-tetraoxo-14,17-dioxa-2,5,8,11-tetraazanonadecanamido)-9-(hydroxymethyl)-1,4,7,10,19-pentaoxo-14,17-dioxa-2,5,8,11,20-pentaazahexacosanamido)-25-(1-(1-(2-(1-(15-amino-1'-(4-aminobutyl)-8-(1-hydroxyethyl)-2,5-diisobutyl- 4,7,10,13-tetraoxo-3,6,9,12-tetraazapentadecane)pyrrolidine-2-carboxamido)-3-hydroxybutanoyl)pyrrolidin-2-yl)-9-(hydroxymethyl)-1,4,7,10-tetraoxo-14,17-dioxa-2,5,8,11-tetraazanonadecanamido)-35-(3-amino-3-oxopropylcarbamoyl)-9-(hydroxymethyl)-1,4,7,10,19,26,33,41-octaoxo-14,17-dioxa-2,5,8,11,20,27,34,40-octaazadotetracontan-42-yl)-1,4,7,10-tetraazacyclododecane-1,4,7-triyl)triacetic acid, indium salt.

Figure 8:
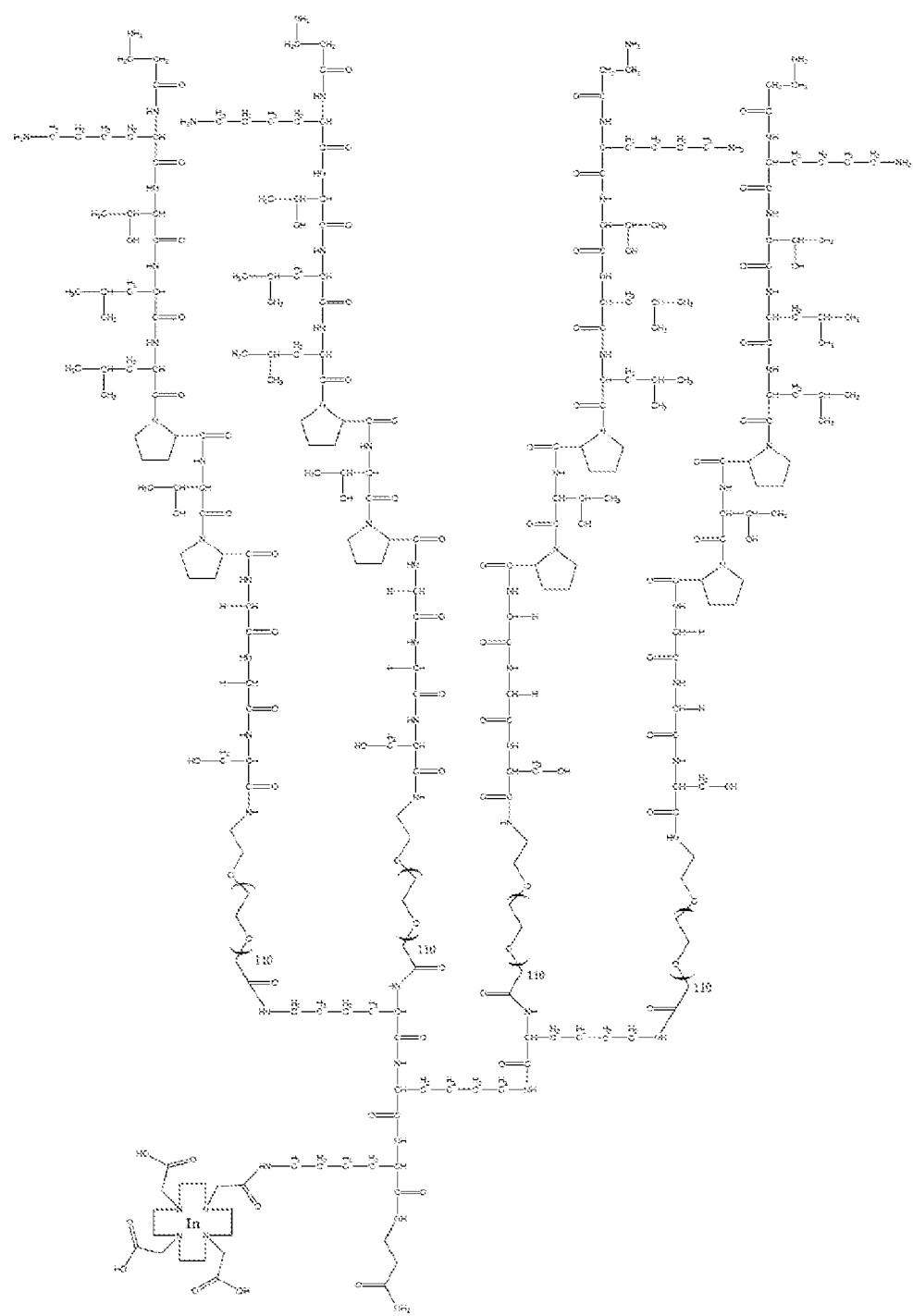
FIG. 8. Chemical structure of tPTP-4(βAKTLLPTPGGS (PEG5000))KKKKDOTAβA-NH$_2$. A chemical structure of the multimeric peptide complex is provided, including an $^{111}$In molecule.

The chemical structure for the above-identified tetrameric formula is (also see FIG. 8):

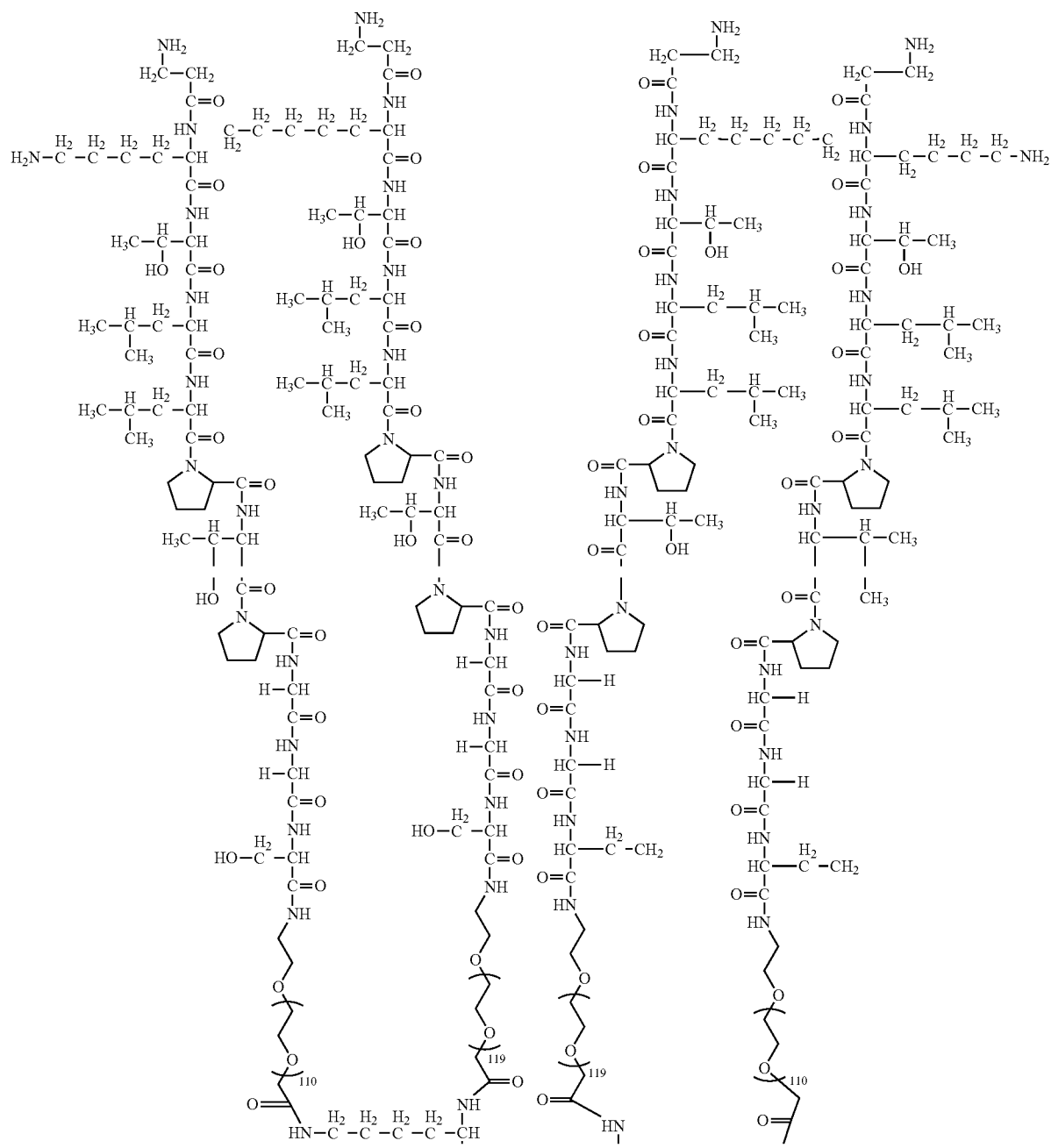

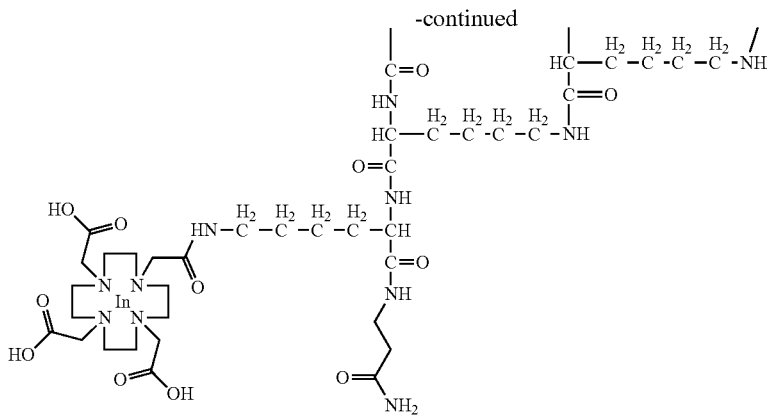

-continued

The present invention further discloses preparation of other multimeric peptide ligand complexes, by, for example, modifying SEQ ID NO:1 or βAKTLLPTPGGS (SEQ ID NO:3). For example, these sequences could be replaced with any of SEQ ID NOs:9-22. Thus, the tetramer of the invention described above, (βAKTLLPTPGGS (PEG5000))₄KKKKDOTAβA-NH₂, is modified by replacing or modifying all or parts of SEQ NO:3 with other sequences which allow for similar properties. As described herein, alanine mutations/substitutions have been made for each of the residues of SEQ ID NO:1, thus other tetramers of the invention include each of those substitutions. Those seven changes encompass seven more tetramers of the invention, namely:

(βAATLLPTPGGS(PEG5000))₄KKKKDOTAβA-NH₂,
(βAKALLPTPGGS(PEG5000))₄KKKKDOTAβA-NH₂,
(βAKTALPTPGGS(PEG5000))₄KKKKDOTAβA-NH₂,
(βAKTLAPTPGGS(PEG5000))₄KKKKDOTAβA-NH₂,
(βAKTLLATPGGS(PEG5000))₄KKKKDOTAβA-NH₂,
(βAKTLLPAPGGS(PEG5000))₄KKKKDOTAβA-NH₂,
and
(βAKTLLPTAGGS (PEG5000))₄KKKKDOTAβA-NH₂,
based on replacing SEQ ID NO:3 with SEQ ID NOs:16-22 respectively.

These are not the only amino acids substitutions encompassed by the invention. Similar substitutions using other amino acids are also encompassed by the invention. Additionally, the data disclosed herein suggest that the presence of threonine may be particularly important, and that proline may be important too. This is evidenced by the fact that their substitutions with alanine did cause at least a slight decrease in affinity. Therefore, the invention further provides, for example, the addition and substitution of the sequences to include more threonine residues or threonine residues at different positions.

The present invention therefore encompasses the preparation of complexes comprising multimers of a peptide ligand, and at least one imaging agent such as a metal, radionuclide, etc., which are typically conjugated to a chelator in order to complex the imaging agent.

In certain embodiments, the imaging agent is attached to the complex by a chelator. In one aspect, the chelator is DOTA.

A number of trivalent metal radionuclides have physical properties suitable for radioisotope imaging (e.g., indium-111 ($^{111}$In), gallium-67/68 ($^{67/68}$Ga) and yttrium-86 ($^{86}$Y) or for targeted radionuclide therapy (e.g., $^{90}$Y and lutetium-177 ($^{177}$Lu)). These metal radionuclides can be combined with a targeting biomolecule (such as a peptide or antibody) in order to diagnose, monitor or treat disease. To obtain a radiolabeled biomolecule with the required stability, the peptide or protein must first be conjugated to a suitable chelator in order to complex the metal. The requirements of chelators for trivalent metals (such as In, Y, Ga and Lu) for labeling peptides are generally the same as those for labeling proteins. The complexes should be stable in biological systems and their chelating ability should not be impaired by reaction with the peptide. Most often, diethylenetriaminepentaacetic acid (DTPA) and/or 1,4,7,10-tetraazacyclododecane-1,4,7,10-tetraacetic acid (DOTA; CAS 60239-18-1) are used (see Choe and Lee, 2007, Current Pharmaceutical Design, 13:17-31; Li et al., 2007, J. Nuclear Medicine, "$^{64}$Cu-Labeled Tetrameric and Octameric RGD Peptides for Small-Animal PET of Tumor avb3 Integrin Expression", 48:1162-1171; Nahrendorf et al, 2009, JACC Cardiovasc. Imaging, 2:10:1213-1222; Li et al., 2009, Mol. Cancer Ther., 8:5:1239-1249; Yim et al., 2010, J. Med. Chem., 53:3944-3953; Dijkgraaf et al., 2010, Eur. J. Nucl. Med. Mol. Imaging, published online 21 Sep. 2010; U.S. patent application Ser. No. 10/792,582; Dransfield et al., U.S. Pat. Pub. Nos. US 2010/0261875; U.S. Pat. No. 7,666, 979). Of the metals mentioned, the DOTA complexes are more thermodynamically and kinetically stable than the DTPA complexes (see Sosabowski et al., Nature Protocols 1, —972-976 (2006) and Leon-Rodriguez et al., Bioconjugate chemistry, Jan. 3, 2008; 19(2):391-402).

Chelating Agents

In some embodiments, a chelating agent may be attached to peptide, directly or indirectly, and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. patent application Ser. No. 12/112,289, which published on Oct. 16, 2008, as US Patent Application Publication Number US 20080253964 A1, which is incorporated herein by reference in its entirety).

Useful chelators encompassed by the invention include, but are not limited to, DTPA, DO3A, DOTA, EDTA, TETA, EHPG, HBED, NOTA, DOTMA, TETMA, PDTA, TTHA, LICAM, HYNIC, and MECAM. HYNIC is particularly useful for chelating Tc99, another imaging agent of the invention.

Modifications

The present invention further provides for the use of molecules such as polyethylene glycol ("PEG") molecules as part of the complex. In one aspect, the PEG is about 20,000 m.w. or about less than about 20,000 m.w. In another aspect, the PEG is less than about 18,000 m.w. In yet another aspect, the PEG is less that about 16,000 m.w. In a further aspect, the PEG is less than about 14,000 m.w. In a further aspect, the PEG is less than about 12,000 m.w. In a further aspect, the PEG is less than about 10,000 m.w. In a further aspect, the PEG is less than about 8,000 m.w. In a further aspect, the PEG is less than about 7,000 m.w. In a further aspect, the PEG is less than about 6,000 m.w. In a further aspect, the PEG is less than about 5,000 m.w. In a further aspect, the PEG is less than about 4,000 m.w. In a further aspect, the PEG is less than about 3,000 m.w. In a further aspect, the PEG is less than about 2,000 m.w. In a further aspect, the PEG is less than about 1,000 m.w. In a further aspect, the PEG is less than about 500 m.w.

In one aspect, the PEG is PEG5000.

Peptide Modification and Preparation

Peptide preparation is described in the Examples. It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicylic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

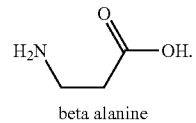

beta alanine

Sequences are provided herein which use the symbol "βA", but in the Sequence Listing submitted herewith "βA" is provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$-, $C_8$- or $C_{18}$- silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of Alkyl-Substituted Hydrophobic Amino Acids:

including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of Aromatic-Substituted Hydrophobic Amino Acids:

including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of Amino Acids Containing Basic Functions:

including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of Acidic Amino Acids:

including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of Side Chain Amide Residues:

including asparagine, glutamine, and alkyl or aromatic substituted derivatives of asparagine or glutamine.

Substitution of Hydroxyl Containing Amino Acids:

including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (O) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Linkers

Additionally, modifications encompassed by the invention include introduction of linkers or spacers between the targeting sequence of the binding moiety or binding polypeptide and the detectable label or therapeutic agent. For example, use of such linkers/spacers can improve the relevant properties of the binding peptides (e.g., increase serum stability, etc.). These linkers can include, but are not restricted to, substituted or unsubstituted alkyl chains, polyethylene glycol derivatives, amino acid spacers, sugars, or aliphatic or aromatic spacers common in the art.

For example, suitable linkers include homobifunctional and heterobifunctional cross-linking molecules. The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde.

Homobifunctional linker molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts.

Heterobifunctional linker molecules have at least two different reactive groups. Some examples of heterobifunctional reagents containing reactive disulfide bonds include N-succinimidyl 3-(2-pyridyl-dithio)propionate (Carlsson et al., 1978. Biochem. J., 173:723-737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate. Other heterobifunctional molecules include succinimidyl 3-(maleimido)propionate, sulfosuccinimidyl 4-(p-maleimidophenyl)butyrate, sulfosuccinimidyl 4-(N-maleimidomethyl-cyclohexane)-1-carboxylate, maleimidobenzoyl-5N-hydroxy-succinimide ester.

Furthermore, linkers that are combinations of the molecules and/or moieties described above, can also be employed to confer special advantage to the properties of the peptide. Lipid molecules with linkers may be attached to allow formulation of ultrasound bubbles, liposomes or other aggregation based constructs. Such constructs could be employed as agents for targeting and delivery of a diagnostic reporter, a therapeutic agent (e.g., a chemical "warhead" for therapy), or a combination of these.

Constructs employing dimers, multimers, or polymers of one or more peptide ligands of the invention are also contemplated. Indeed, there is ample literature evidence that the binding of low potency peptides or small molecules can be substantially increased by the formation of dimers and multimers. Thus, dimeric and multimeric constructs (both homogeneous and heterogeneous) are within the scope of the instant invention. The polypeptide sequences in the dimeric constructs can be attached at their N- or C-terminus or the N-epsilon nitrogen of a suitably placed lysine moiety (or another function bearing a selectively derivatizable group such as a pendant oxyamino or other nucleophilic group), or can be joined together via one or more linkers (e.g., those discussed herein) employing the appropriate attachment chemistry. This coupling chemistry can include amide, urea, thiourea, oxime, or aminoacetylamide (from chloro- or bromoacetamide derivatives, but is not so limited). For example, methods to prepare dimeric or multimeric constructs of Plec1 binding polypeptides of the invention include at least those discussed below.

Linkers can also be used for attachment to a chelating agent.

Therapeutic Agents

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the multimeric peptide ligand complexes described herein. Drugs useful in the invention may, for example, possess a pharmaceutical property selected from the group consisting of antimitotic, antikinase, alkylating, antimetabolite, antibiotic, alkaloid, anti-angiogenic, pro-apoptotic agents and combinations thereof.

Diagnosing, Monitoring, and Treating Cancer

In another aspect, the invention provides compositions and methods for diagnosing a cancer in a subject. The methods include providing a sample, e.g., a biopsy sample, from a patient, and a diagnostic composition including a multimeric peptide ligand complex, wherein the peptide ligand(s) sequence is selected from, in one aspect, one of SEQ ID NOs:1-4 and 9-22, optionally conjugated to a detectable moiety, adding the peptide to the sample, and detecting the diagnostic composition, e.g., by detecting the detectable moiety in the sample. In some embodiments, the imaging includes but is not limited to laser scanning microscopy, immunohistochemistry, fluorescent microscopy, radiographic imaging and the like.

In a further aspect, the invention provides in vivo methods and compositions for diagnosing a cancer. The methods include identifying a subject at risk for or suspected of having pancreatic cell cancer; administering to a subject a diagnostic composition comprising a multimeric peptide ligand complex of the invention conjugated to an imaging molecule, and imaging the imaging molecule within the subject using in vivo imaging. In some embodiments, the pancreatic cell cancer is a pancreatic ductal adenocarcinoma. In some embodiments, the imaging molecule is a magnetofluorescent particle. In some embodiments, the magnetofluorescent particle comprises a near infrared (NIR) fluorochrome (NIRF). In some embodiments, the composition is administered via route selected from the group consisting of intradermal, subcutaneous, intraperitoneal, intravenous, intraarterial, oral, and gastric routes. In some embodiments, the in vivo imaging includes but is not limited to magnetic resonance imaging (MRI), intravital laser scanning microscopy, endoscopy, SPECT/CT, and radiographic imaging.

The invention further provides for monitoring the progression of cancer, including during carcinogenesis. The present application discloses that Plectin-1 expression and cellular localization change during pancreatic carcinogenesis. The present invention provides compositions and methods for monitoring these changes.

In one embodiment, the present invention further provides compositions and methods for monitoring the progression or treatment of a cancer.

In another embodiment, the present invention provides methods for surgically removing pancreatic cancer cells. The methods include a) providing: i) a composition comprising a multimeric peptide ligand complex of the invention for distinguishing a pancreatic cancer cell from a pancreatic non-cancer cell; ii) a subject known to have pancreatic cancer; iii) an in vivo imaging device; and b) administering the composition to a subject; c) imaging pancreatic cancer cells in vivo with the imaging device; and d) removing pancreatic cancer cells from the subject following detecting their location.

The present invention provides a method of treating a patient with cancer, comprising, a) providing: i) a subject in need of treatment; ii) a pharmaceutical composition comprising a multimeric peptide ligand complex of the invention, wherein the ligand binds to a biomarker of the present invention; and b) administering the treatment composition to the subject. In some embodiments, the pharmaceutical composition further comprises a therapeutic agent. In some embodiments, the therapeutic agent is selected from the group consisting of at least one fusion protein, a toxin, and a drug, or a combination thereof.

The present invention is not limited by the type of cancer expressing Plectin-1 or a fragment or homolog thereof or exhibiting cell surface plectin-1. Indeed, various types of cancer are contemplated for use with the detection methods of the present inventions including, but not limited to lung cancer, bladder cancer, head and/or neck cancer, breast cancer, esophageal cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, stomach cancer, prostate cancer, testicular cancer, ovarian cancer; cervical cancer, endometrial cancer, uterine cancer, pancreatic cancer, colon cancer, colorectal, gastric cancer, kidney cancer, bladder cancer, lymphoma cancer, spleen cancer, thymus cancer, thyroid cancer, brain cancer, neuronal cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, white blood cell cancer (e.g., lymphoma, leukemia, etc.), hereditary non-polyposis cancer (HNPC), colitis-associated cancer, etc. Cancers are further exemplified by sarcomas (such as osteosarcoma and Kaposi's sarcoma).

The present invention provides a method of treating a patient with pancreatic cancer, comprising, a) providing, i) a cancer patient in need of treatment, ii) a pharmaceutical composition comprising a ligand, wherein the ligand binds to plectin-1 or a fragment thereof, and b) administering the treatment composition to the patient. In some embodiments, the pharmaceutical composition further comprises a therapeutic agent. In some embodiments, the therapeutic agent is selected from the group consisting of a fusion protein, a toxin, and a drug. In an additional aspect, the present invention provides methods of treating a subject who has pancreatic cancer. The methods include identifying a subject in need of treatment, e.g., on the basis that they have pancreatic cancer, and administering a therapeutically effective amount of a pharmaceutical composition including a multimeric peptide ligand complex, including, but not limited to peptides having the sequence SEQ ID NOs:1-4 and 9-22, linked to a cytotoxic agent, e.g., a toxin or a drug.

In another aspect, the present invention provides methods for identifying a cancer cell-binding partner (receptor) having selective affinity for a peptide ligand. The methods include selectively immobilizing a diverse population of binding molecules to a solid support, contacting (e.g., simultaneously contacting) the diverse population immobilized on the solid support with one or more peptide ligands and determining at least one binding molecule which selectively binds to one or more of the peptide ligands, including those expressed by a bacteriophage. Also provided are methods for identifying peptide ligands having selective affinity for a tumor antigen (binding molecule). The methods include selectively immobilizing a tumor antigen to a solid support, contacting (e.g., simultaneously contacting) the immobilized tumor antigen on the solid support with one or more peptide ligands and identifying at least one peptide ligand which selectively binds to one or more of the tumor antigens. Also provided are isolated binding peptides ("peptide ligands") that are selective for a tumor biomarker, in particular peptide ligands for plectin-1. Also described herein are rapid and efficient methods for the identification of binding molecules that exhibit selective affinity for one or more peptide ligands of interest. The methods are advantageous in that they allow the simultaneous screening of multiple binding molecules against multiple peptide ligands of interest. Moreover, very little information is required regarding the identity or function of either the binding molecule or the ligand for use in the present inventions. For example, diverse populations of binding molecules can be simultaneously screened against diverse populations of peptide ligands to rapidly identify numerous molecules exhibiting a desired binding specificity. The methods described herein can therefore be advantageously applied for the discovery of specific reagents, such as peptide ligands and biomarkers, for diagnosis and treatment of human diseases.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

Imaging and Diagnostic Agents

Diagnostic agents are selected from, for example, the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerythrin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Techniques for detecting and measuring these agents are provided in the art or described herein.

Antibodies and their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

Aptamers

The present invention is also directed to useful aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

The present invention also encompasses pharmaceutical and therapeutic compositions comprising the multimeric peptide ligand complexes of the present invention. More particularly, such compounds can be formulated as pharmaceutical compositions using standard pharmaceutically acceptable carriers, fillers, solublizing agents and stabilizers known to those skilled in the art.

The present invention further provides a pharmaceutical preparation comprising one or more of the multimeric peptide ligands or complexes of the invention. The concentration of said polypeptide in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the peptides o to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

Methods of producing pharmaceutical compositions comprising polypeptides are described in U.S. Pat. Nos. 5,789, 543 and 6,207,718. The preferred form depends on the intended mode of administration and therapeutic application.

In one embodiment, the present compositions comprising multimeric peptides are administered by injection. The parenteral route for administration of the polypeptide is in accordance with known methods, e.g. injection or infusion by intravenous, intraperitoneal, intramuscular, intra-arterial, subcutaneous, or intralesional routes. The protein or polypeptide may be administered continuously by infusion or by bolus injection. A typical composition for intravenous infusion could be made up to contain 10 to 50 ml of sterile 0.9% NaCl or 5% glucose optionally supplemented with a 20% albumin solution and between 10 ug and 50 mg, preferably between 50 ug and 10 mg, of the polypeptide. A typical pharmaceutical composition for intramuscular injection would be made up to contain, for example, 1-10 ml of sterile buffered water and between 10 ug and 50 mg, preferably between 50 ug and 10 mg, of the polypeptide of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

Pharmaceutical Compositions and Administration

The invention is also directed to methods of administering the compounds of the invention to a subject. In one embodiment, the invention provides a method diagnosing cancer, detecting Plec-1, localizing Plec-1 expressing cells, or treating a subject by administering compounds identified using the methods of the invention description. Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present invention to a subject in need thereof. Compounds identified by the methods of the invention can be administered with known compounds or other medications as well.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

The invention also includes a kit comprising the composition of the invention and an instructional material which describes adventitially administering the composition to a cell or a tissue of a subject. In another embodiment, this kit comprises a (preferably sterile) solvent suitable for dissolving or suspending the composition of the invention prior to administering the compound to the subject.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the invention may, for example, be affixed to a container which contains the multimeric peptide of the invention or be shipped together with a container which contains the peptide. Alternatively, the instructional material may be shipped separately from the container with the intention that the instructional material and the compound be used cooperatively by the recipient.

Other techniques known in the art may be used in the practice of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

Examples

The experiments described below were designed to determine if Plectin-1 (PLEC-1) is a biomarker for cancers, particularly preinvasive, invasive and metastatic PDAC and to develop better ligand complexes for detecting Plectin-1. Furthermore, it was sought to determine if it distinguishes benign, most importantly chronic pancreatitis, from malignant pancreatic disease and if its overexpression can be exploited for non-invasive imaging of PDAC. Additionally, it was evaluated herein whether Pled also is a biomarker in other, non-pancreatic human cancers.

Methods:
Tissue Samples

All tissues and biologic samples were collected with the approval and in accordance with the requirements of an Institutional Review Board.

Paraffin-embedded tissue samples were obtained from hospital files. All specimens had an established diagnosis at the time of assessment. A total of 4 normal pancreata, 15 chronic pancreatitis, 14 PanIN I, 26 PanIN II, 15 PanIN III and 31 PDAC, 8 liver metastasis, 1 lymph node metastasis and 1 peritoneal metastasis were obtained. For the assessment of Plec1 expression in extra-pancreatic human cancer, a commercial tumor tissue microarray (MTU951, US Biomax, Rockville, Md.) was used.

Mice

All animal procedures were approved. Athymic female mice (nu/nu) were obtained from an in-house breeding facility. Mice were maintained in a germ-free environment and had access to food and water available ad libitum.

Western Blot Analysis 50 mg of pancreatic tissue obtained as snap frozen surgical specimens was homogenized in RIPA-buffer (50 mM Trizma Base, pH 7.4, 1% Triton X-100, 0.25% Natriumdesoxycholat, 100 mM EDTA 150 mM NaCl) in combination with a protease inhibitor cocktail (0.001 mg/ml Aprotinin, Bestatin, Pepstatin, Leupeptin and 0.005 mg/ml 20 mM PMSF, Sigma-Aldrich, St. Louis, USA). The lysate was cleared by centrifugation and protein concentration determined using a very precise assay (2-D Quant Kit, Amersham Biosciences, NJ). 20 µg protein/lane were separated via SDS-PAGE and transferred onto a nitrocellulose membrane. Antigen detection was performed using a rabbit monoclonal antibody against human Plec1 (Abcam, Cambridge, Mass.). The secondary antibody was a HRP-coupled goat anti-rabbit polyclonal antibody (Sigma-Aldrich, St. Louis, USA). Bands were visualized with ECL. (control: rat brain lysate, Santa Cruz Biotechnology, La Jolla, Calif.).

Immunostaining

Paraffin-embedded sections were deparaffinized, hydrated with TBS and blocked with $H_2O_2$. Antigen retrieval was achieved by boiling tissue in Retrievit (BioGenex, San Ramon, Calif.). After blocking with avidin/biotin (Vector Laboratories, Burlingame, Calif.) and 5% goat serum in TBS, slides were incubated overnight at 4° C. with 1:250 Plec1 antibody (Abcam). Sections were washed three times in TBST, followed by incubation with biotinylated anti-rabbit goat secondary antibody (Vector Laboratories, Burlingame, Calif.), then developed using DAB (Invitrogen, Carlsbad, Calif.) and counterstained with hematoxylin. Slides were evaluated using a Y-FL microscope (Nikon, Japan). Images were acquired with a DP-25 camera and acquisition software (Olympus, Japan).

Histological Assessment

Nerves were noted to have moderate staining intensity for Plec1 and were present on all slides. Expression of Plec1 in nerves within each slide was therefore used as a staining control and reference for staining intensity. Staining intensity was recorded by two independent observers, and in case of discrepant results, evaluated by a third observer. Staining of abnormal epithelial cells was classified relative to the moderate staining seen in nerves as negative, weak, moderate or strong.

In Vitro Competition Assay

A tetrameric plectin-1 targeted peptide (tPTP) complex, (βAKTLLPTPGGS(PEG5000))$_4$ KKKKDOTAβA-NH$_2$, (also referred to as [(βAla-Lys-Thr-Leu-Leu-Pro-Thr-Pro-Gly-Gly-Ser-PEG5K)$_2$-Lys]$_2$-Lys-Lys(DOTA)-βAla-NH$_2$ herein) was synthesized in a GMP grade facility (CS Bio Company, Menlo Park, Calif.), based on the plectin-1 targeting peptide KTLLPTP (SEQ ID NO:1) (Kelly et al., 2008, PLoS Medicine, 5:4:e85:0657-0668).

Summary for Production of the tPTP Branched PEG Peptide Complex:

Peptide Sequence (Example)—
[(βAla-Lys-Thr-Leu-Leu-Pro-Thr-Pro-Gly-Gly-Ser-PEG5K)$_2$-Lys]$_2$-Lys-Lys(DOTA)-βAla-NH2
MW: 25648
PEG5K: is from Fmoc-PEG5000-NHS Ester (JenKem Tech)

Material—
1) Resin:
Fmoc-Rink-Amide Resin (Sub: 0.34 mmol/g);
2) The special side-chain protected AAs were used as follows:
Lys-15: Lys(Mmt), Lys-14, 13: Fmoc-Lys(Fmoc);
3) Coupling Reagent: Rx/AA/DIC/HOBt (1/3/3/3);
4) Cleavage Reagent: TFA/TIS/H2O;
5) Purification: ACN/H2O/TFA Synthesis—
1) Attached β-Ala to the Rink amide resin, and after de-Fmoc of β-Ala on Rx, Fmoc-Lys(Mmt) was attached.
2) With Fmoc group on, De-Mmt and coupled Tri-tBu-DOTA to Lys-15 side chain. Coupling: Rx/DOTA/DIC/HOBt (1/2/2/2), single coupling.
3) After De-Fmoc, Fmoc-Lys(Fmoc) was attached to the extended peptide on Rx. Executed DeFmoc on Lys-14, which would leave two free NH2- groups, one on the main chain, and the other on side chain.
4) Used double amount of coupling reagent to attach Fmoc-Lys(Fmoc) to two NH$_2$— groups on the Rx. After deFmoc, four NH$_2$— groups on Rx were available for the next coupling.
5) Fmoc-PEG5000-NHS was then attached to the four NH$_2$— groups using DIPEA as promoter (Rx/PEG 1/8). After a negative Kaiser test, DeFmoc of PEG and continued AA coupling one by one to the 4 branched N-terminals till β-Ala-1.
6) After final deFmoc, the Rx was ready for cleavage.

Cleavage—
Reagent:
95% TFA, 2.5% H2O, 2.5% TIS. Stirred for 240 min at room temperature.
Removed solvents from the reaction using vacuum and lyophilized the mixture after addition of water/ACN.

Purification—
Crude peptide (as syrup) was loaded onto HPLC column (4.1×25 cm×cm) after dilution with water and purified in a gradient of 20-60% buffer B in 60 min Flow rate, 25 mL/min in TFA buffer system. A 0.1 mmol synthesis gave 200 mg final product. (Not optimized)

DOTA (1,4,7,10-tetraazacyclododecane-1,4,7,10-tetraacetic acid) has the structure:

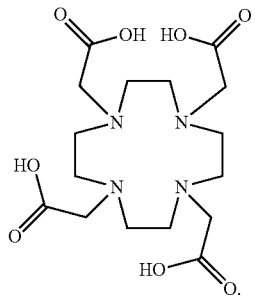 [SMILES: O=C(O)CN1CCN(CC(=O)O)CCN(CC(=O)O)CCN(CC(=O)O)CC1]

As a control, a non-binding tetramer (ncPTP-4(βAKHVMSKQGGS (PEG5000))KKKDOTAβA-NH$_2$) was also synthesized. Sequences of the control peptides include KHVMSKQ (SEQ ID NO:5) and SEQ ID NO:5 with two glycines and a serine added, giving rise to KHVMSKQGGS (SEQ ID NO:6). A beta alanine (βA) added to SEQ ID NO:5 or to SEQ ID NO:6 gives rise to βAKHVMSKQ (SEQ ID NO:7) and βAKHVMSKQGGS (SEQ ID NO:8), respectively.

The tPTP was chemically synthesized in a GMP facility as a tetramer to increase multivalency, and four 5000 Da PEG chains (one to each peptide of the four peptides) were added to increase the circulation time of the agent, to reduce immunogenicity, and to protect the peptide from becoming cleaved in vivo before reaching the intended target.

Adding an Imaging Agent

For Indium labeling, peptide (100 μg, nmoles) was dissolved in 20 μL PBS, then diluted in 100 μL ammonium acetate buffer (0.1M, pH 4.5). Indium Chloride (5 mCi in water) (Cardinal Health, VA) was mixed with the peptide and allowed to equilibrate with mixing at 40° C. for 15 min. The reaction mixture was purified by size exclusion using a PD10 desalting column pre-equilibrated with DPBS. For in vitro peptide validation experiments, cells were incubated at room temperature for 1 hr with tPTP or ncPTP with concentrations ranging from $10^{-3}$ to $10^{-9}$ and 5 μCi tPTP-In$^{111}$ in triplicate. After 1 hr the cells were washed and lysed with 100 μL 1M NaOH for 5 min. The mixture was then transferred to tubes and counts analyzed on a gamma counter.

Imaging

Mice (n=4) bearing orthotopically injected L3.6 μl pancreatic cancer tumor cells were injected with 1 mCi of $^{111}$In labeled tPTP, then imaged 4 hours post injection with a microSPECT/CT scanner designed and built at UVa. Anesthesia (1%-2% isoflurane in oxygen) was delivered throughout the imaging. CT acquisition used 200 evenly spaced projections spanning 200 degrees over approximately 5 minutes. Mice are repositioned axially for pinhole SPECT scanning 60 evenly spaced projection views were obtained over 180 degrees using two gamma cameras simultaneously. The acquisition time was approximately 30 minutes. The two cameras were fitted with 1 mm diameter tungsten pinholes. The reconstructed CT voxel size was 0.082×0.082×0.082 mm on a 512×512×640 image matrix. The reconstructed SPECT voxel size was 0.65×0.65×0.65 mm on a 60×60×60 image matrix. All SPECT images were corrected for radioactivity decay but not for gamma ray attenuation.

Biodistribution and Blood Half-Life

After mice were imaged via SPECT/CT, animals were sacrificed and their organs harvested and placed into pre-weighed Eppendorf tubes. Each tube was then re-weighed to determine the weight of the organ and the radiation measured. To determine the plasma lifetime of the probe, a mouse injected with the tPTP-Peg-$^{111}$In was bled 0, 15, 30, 45, 60, and 120 min post injection, and the radioactivity measured via well counter.

Histology

PDAC specimens from the pancreas and the peritoneal metastases were fixed with 4% PFA and frozen in OCT. The tissues samples were then sliced and stained via H&E.

Alanine Mutation of Panc 27 Peptide (KTLLPTP (SEQ ID NO:1))

The effect of alanine substitutions of each of the amino acids residues of SEQ ID NO:1 was determined. The peptides used in this study consist of the phage derived sequence KTLLPTP (SEQ ID NO:1) and the alanine mutations ATLLPTP, KALLPTP, KTALPTP, KTLAPTP, KTLLATP, KTLLPAP, and KTLLPTA, SEQ ID NOs:9-15, respectively, where each residue was sequentially mutated to an alanine. Two mg of each peptide was dissolved in 200 µL PBS, mixed with 1 mg FITC, and allowed to react overnight. The peptides were purified by flash chromatography on C18 reverse phase resin using acetonitrile/water mixtures and quantitated by spectroscopy.

L3.6 cells were plated on 24 well plates and used when approximately 90-95% confluent. The peptides were diluted to 30 µM, then a concentration series made by diluting down by 3, with the lowest concentration approximately 14 nM (8 concentrations). These were placed on the L3.6 cells (200 µL/well in triplicate) and allowed to incubate on ice for 2 hrs. They were washed 3 times with PBS+1% Tween-20, and lysed in 200 µL of lysis buffer (50 mL PBS, 0.5 mL Triton X-100, 15 mg ANSA (amino napthaleno sulfonic acid) and 20 uL of an anti-FITC antibody labeled with HRP. To quantitate the amount of peptide remaining, the lysates were incubated 1 hr at 37° C. on an immunoassay plate labeled with FITC-BSA, along with peptide dilutions for a standard curve. The plates were washed 4-5 times with a solution of 0.1% BSA and 0.1% Tween-20 in PBS, and developed with tetramethylbenzidine.

The absorbance vs. concentration curves from these studies were analyzed using Graphpad prism as a sigmoidal dose-response (variable slope) curve to calculate the apparent affinity of the peptide. The entire procedure was repeated at least once to verify the affinity of each mutation, and experiments that did not fit the expected sigmoidal dose-response curve were re-run.

Results

Plec1 is Expressed in PDAC, but not in Chronic Pancreatitis and Normal Pancreas

Plec1 expression clearly distinguishes malignant from benign pancreatic disease (FIG. 1). One hundred percent of PDAC (31/31) stained for Plec1; 77% (24/31) stained strongly, 23% stained moderately (7/31). In contrast to PDAC, Plec1 was identified neither in the normal pancreas (4/4) nor in the majority of chronic pancreatitis (10/15). The remaining chronic pancreatitis (5/15) stained weakly for Plec1 in the ductal epithelium (FIG. 1B). Western blotting of pancreatic tissue lysates confirmed the IHC findings. No Plec1 was detected in the normal pancreas (2/2) and chronic pancreatitis (3/3) whereas it was present in each PDAC (3/3; FIG. 1D).

Plec1 Expression and Cellular Localization Change During Pancreatic Carcinogenesis Plec1 expression intensity increases during pancreatic carcinogenesis (FIG. 1). As lesions progress from PanIN I to III, their staining intensity for Plec1 increases and an increasing percentage of lesions becomes Plec1 positive. Early stage PDAC precursor lesions, PanIN I, are mostly Plec1-negative (11/14). In contrast, more than half of the PanIN II lesions expressed Plec1 weakly (13/26) or moderately (1/26), while 87% of PanIN III lesions were Plec1-positive (13/15; FIG. 1 A, B). Notably, the cellular localization of Plec1 also changes during carcinogenesis. If Plec1 was identified in an early PanIN lesion, its localization was restricted to the cell membrane while Plec1 expression in malignant lesions had a cytoplasmic and membranous localization. Plec1 localized to the membrane and cytoplasm in 27% (4/15) of the pre-invasive malignant PanIN III and 100% (31/31) of invasive PDAC lesions (FIG. 1 C).

Plec1 Expression is Retained in PDAC Metastasis

PDAC has a propensity to metastasize early to the peritoneum, lymph nodes, and liver, where Plec1 is not normally expressed. All metastatic foci assayed retained their Plec1 expression (8/8 liver, 1/1 lymph node and 1/1 peritoneal metastasis), clearly identifying and highlighting metastatic deposits in these tissues (FIG. 1A).

Plec1 is Overexpressed in Non-Pancreatic Human Cancers

Figure 2:
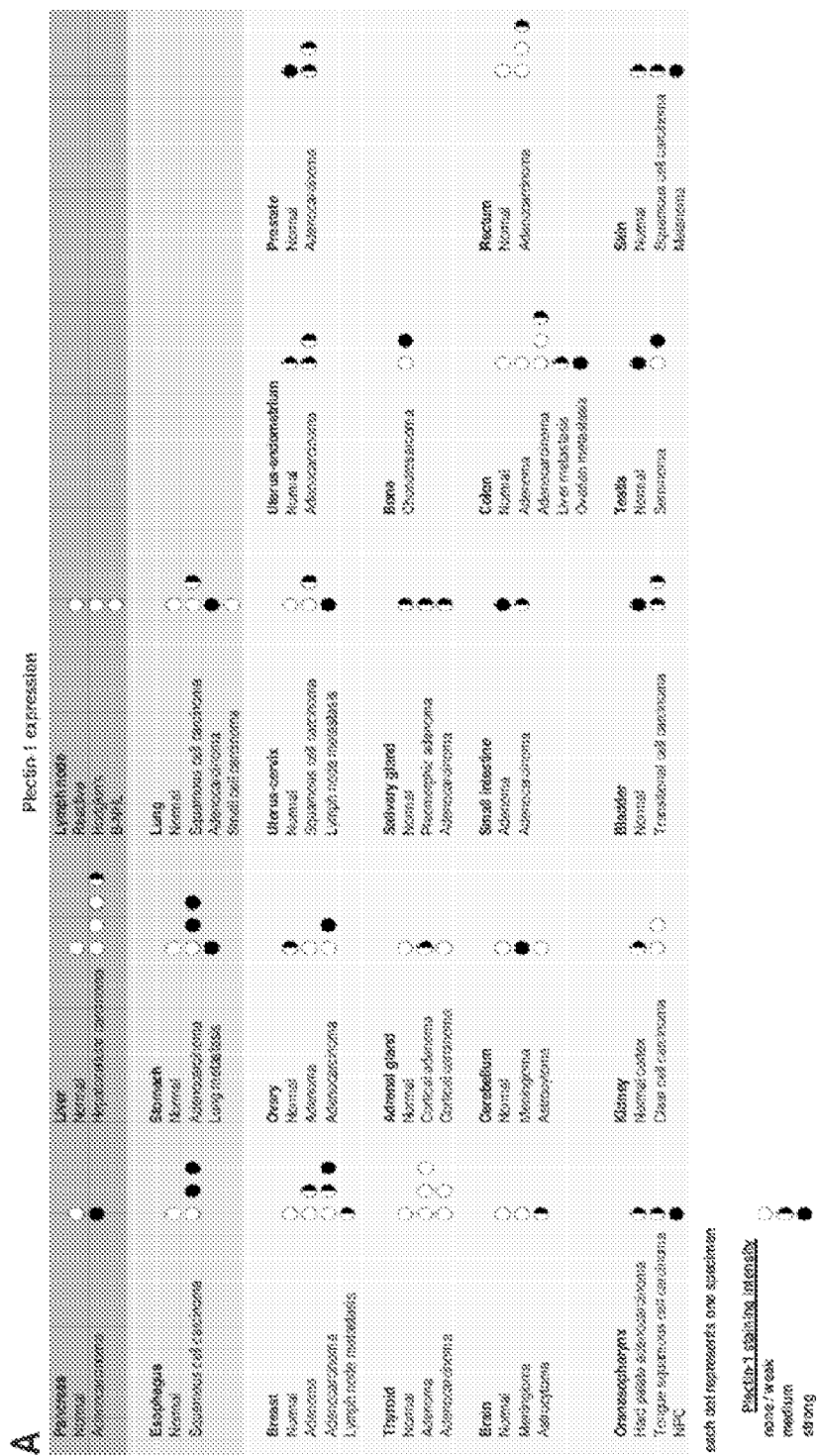
FIG. 2: Plectin-1 expression in normal and malignant human tissue: Immunohistochemistry of a tissue microarray evaluated for Plectin-1 expression: Normal tissue shows only a weak to moderate Plectin-1 expression with the exception of bladder and male reproductive tract. A clear difference in Plectin-1 expression distinguishing normal from malignant disease is only observed in the pancreas, esophagus, stomach and lung. Common PDAC metastasis sites (lymph node, liver) do not express Plec1.

IHC of a human tumor tissue microarray revealed that the utility of Plec1 may not be limited to pancreatic cancer. In esophagus, stomach, and lung specimens, Plec1 also had a differential expression pattern, which can potentially be used to distinguish benign from malignant tissue (FIG. 2).

Plec1 Targeting Probes can be Used for Non-Invasive Imaging of PDAC

Figure 3A:
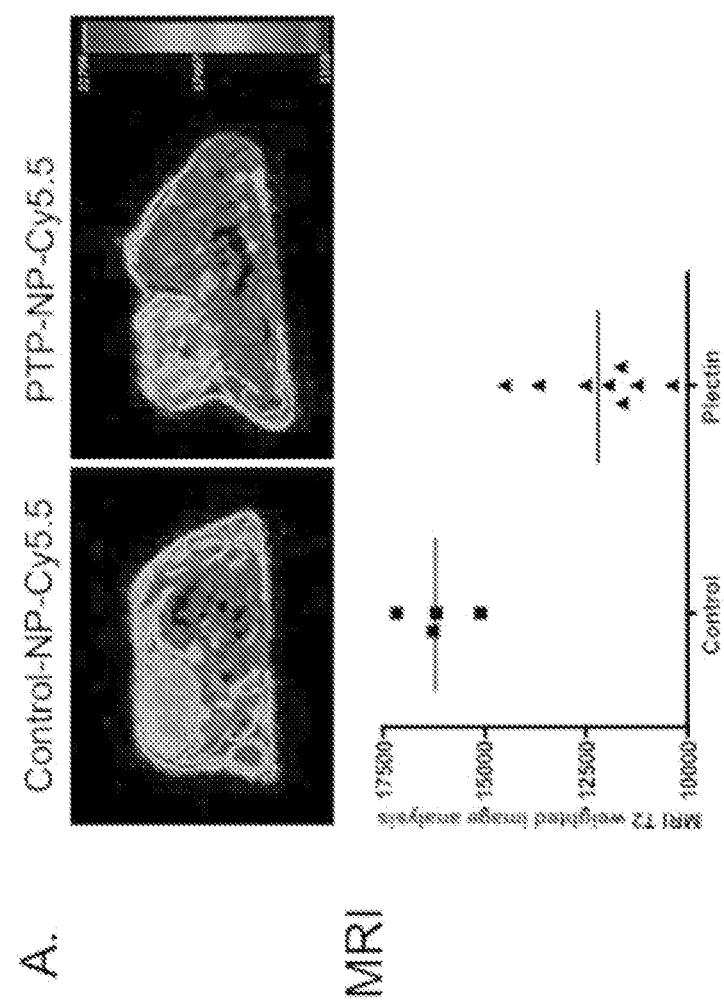
FIG. 3: In vivo imaging of Plec1 in orthotopic PDAC. (A). In vitro validation of tPTP. L3.6 cells were plated on a 96 well plate and incubated with 111In-tPTP and increasing log concentrations of tPTP or scrambled tetramer. (B). Athymic nude mice bearing tumors from orthotopically implanted L3.6 cells were injected with 111In-tPTP and imaged via SPECT/CT 4 hours post injection. Note the accumulation of tPTP in PDAC, allowing the in vivo imaging of tumor in the pancreas and in peritoneal metastases. T—Tumor, L, Liver, rK—right Kidney, lK—left Kidney, M—peritoneal metastasis. (C). After SPECT/CT imaging (FIG. 3) animals (n=5) were sacrificed, organs harvested and gamma counts assessed. (D). Histology. Animals that had orthotopically implanted tumors were sacrificed and pancreas and regions of visible peritoneal metastases were removed, embedded in OCT, sectioned and stained with H&E. A. 10× image of tumor in the pancreas. Inset, 2× view of pancreas showing two tumors. B. 10× image of peritoneal metastasis. Inset, 2× image of metastasis and surrounding peritoneum.
Figure 3B:
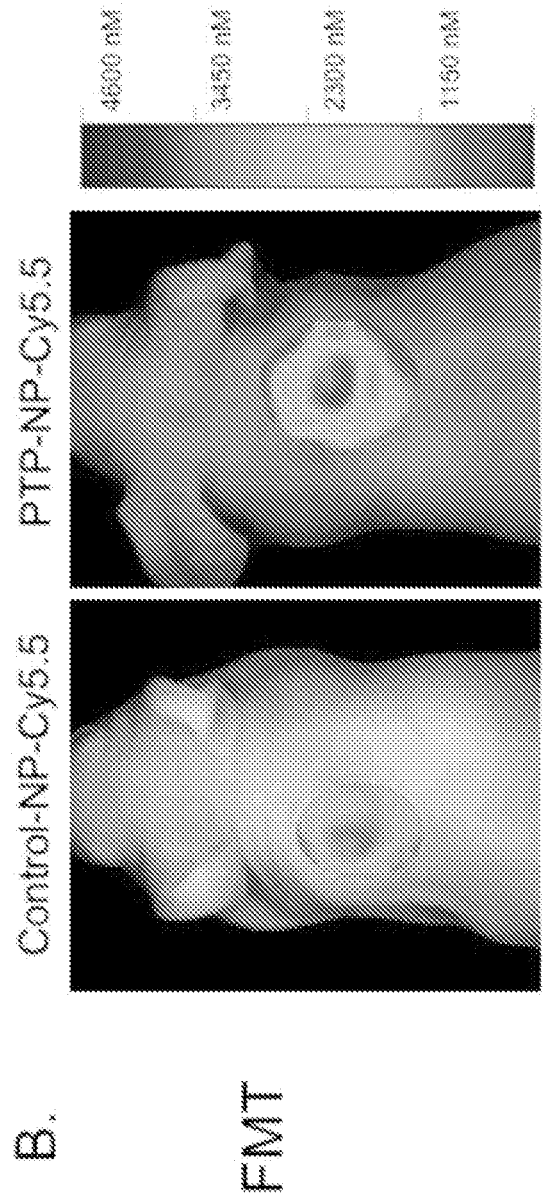
Figure 4:
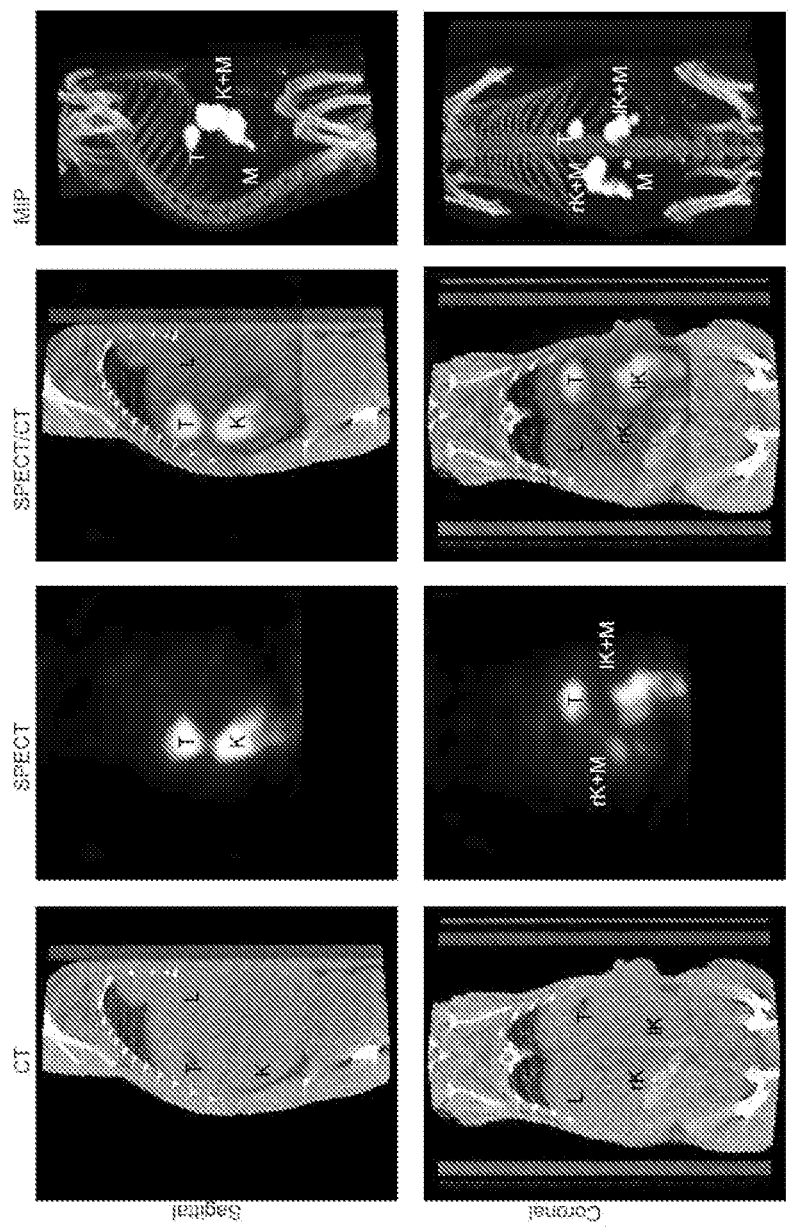
FIG. 4. tPTP targets PDAC and enables non-invasive in vivo imaging. Athymic nude mice bearing tumors from orthotopically implanted L3.6 cells were injected with $^{111}$IN-tPTP and imaged via SPECT/CT 4 hours post injection. SPECT/CT imaging demonstrates that tPTP accumulates in PDAC, allowing the in vivo imaging of tumor in the pancreas and in peritoneal metastases. T—Tumor; L—Liver; rK—right Kidney; lK—left Kidney; M—peritoneal metastasis. Upper panels—Sagittal plane of view; Lower panels—Coronal plane of view. Left two images—CT; Second from left—SPECT; Third from left—SPECT/CT; Right two images—MIP. (See also FIG. 3).

To determine whether Plec1 could function as an imaging biomarker to facilitate the in vivo detection of human PDAC, we employed Plec1-targeted peptides derived from a phage display screen to synthesize a tetrameric synthetic peptide (tPTP) complex (see FIG. 8) that functions as a clinically relevant imaging agent for single photon emission computed tomography (SPECT). In vitro validation of the specificity of the tPTP was performed by competition assay with labeled tPTP and unlabeled tPTP or negative control PTP (ncPTP). The Ki (inhibition dissociation constant) for tPTP was $8.3 \times 10^{-7}$ M vs $2.86 \times 10^{-6}$ M for ncPTP (FIG. 3A). Animals with orthotopic injection of pancreatic cancer cells were administered tPTP and imaged via SPECT/CT 4 hours later. Imaging illuminated not only the tumor in the pancreas but also metastases present in the peritoneum of the animals (FIG. 3B and FIG. 4). Biodistribution studies performed after imaging demonstrated that the pancreatic tumors had a 3% injected dose/gram (id/g) of tissue, while spleen, liver, and heart had less than 1% id/g (FIG. 3C). The probe also accumulated in the kidneys; indeed the main route of elimination of this peptide was through the kidneys (FIG. 3C) and the urine. H&E staining of sectioned pancreas and peritoneum demonstrated the presence of tumors in the pancreas and also metastases in the peritoneum (FIG. 3D). These data show that tPTP functions as a highly specific imaging tool for plectin-1.

tPTP Targets PDAC and Enables Non-Invasive In Vivo Imaging

Athymic nude mice bearing tumors from orthotopically implanted L3.6 cells were injected with $^{111}$IN-tPTP and imaged via SPECT/CT 4 hours post injection. SPECT/CT imaging demonstrates that tPTP accumulates in PDAC, allowing the in vivo imaging of tumor in the pancreas and in peritoneal metastases. See FIG. 4.

Figure 5:
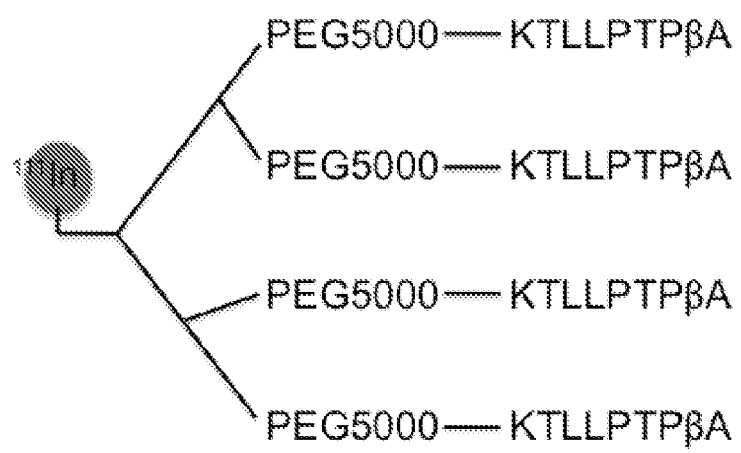
FIG. 5. Schematic illustration of Plectin-1 Targeted peptide. A highly schematized version of a multimeric peptide ligand complex comprising four copies of SEQ ID NO:1 to increase multivalency, and depicting four 5000 Da PEG chains, which can be added to increase the circulation time of the agent, to reduce immunogenicity, and to protect the peptide from becoming cleaved in vivo before reaching the intended target. Other potential modifications are not shown.
Figure 7:
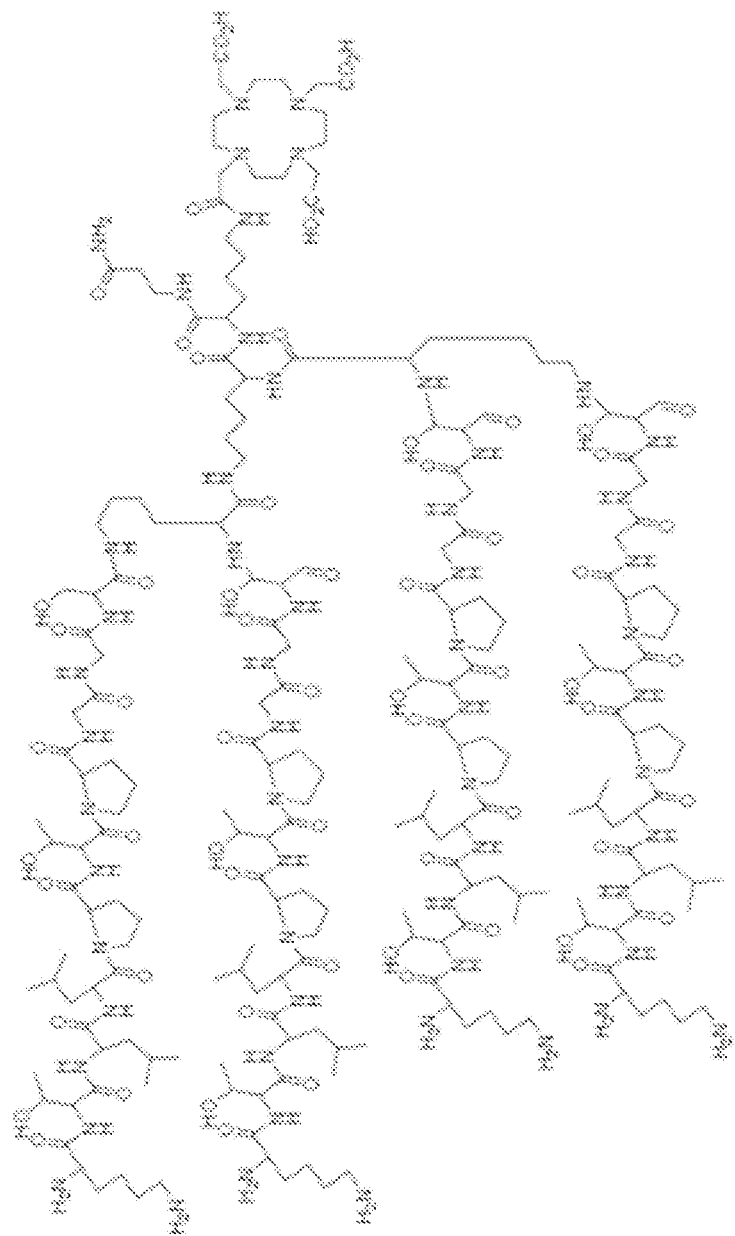
FIG. 7. [Lys-Thr-Leu-Leu-Pro-Thr-Pro-Gly-Gly-Ser]$_4$-Lys$_4$-βAla-DOTA. Chemical structure of the tetrameric complex having the formula [Lys-Thr-Leu-Leu-Pro-Thr-Pro-Gly-Gly-Ser]$_4$-Lys$_4$-βAla-DOTA, also referred to as [KTLLPTPGGS]$_4$-K$_4$-βA-DOTA.

FIG. 5 is a schematic illustration of a tetrameric plectin-1 targeted peptide. FIG. 7 is another tetrameric plectin-1 tetrameric peptide.

In Vivo Characterization of tPTP

Figure 6:
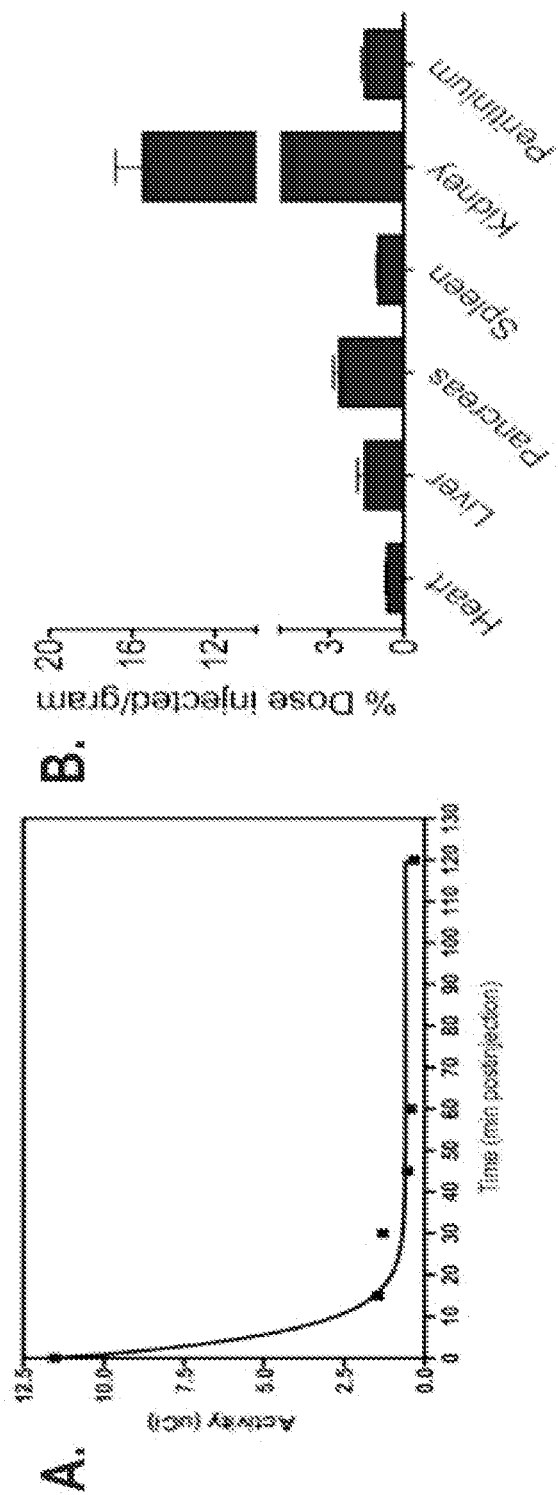
FIG. 6. In vivo characterization of tPTP—6A. Blood half-life of $^{111}$IN-tPTP injected into athymic nude mice bearing tumors from orthotopically placed L3.6 cells. Blood was taken at 0, 15, 30, 45, 60, and 120 minutes post injection. The blood half-life of tPTP was 4.29 minutes. 6B. After SPECT/CT imaging (See FIG. 4) animals (n=5) were sacrificed, organs harvested, and gamma counts assessed. The pancreas showed a 3% injected dose/gram while the metastasis found in the peritoneal cavity showed a 1.5% injected dose/gram. The primary route of excretion of $^{111}$IN-tPTP is through the urine.

FIG. 6 demonstrates the results blood half-life studies of $^{111}$IN-tPTP injected into athymic nude mice bearing tumors from orthotopically placed L3.6 cells (See FIG. 6A). Blood was taken at 0, 15, 30, 45, 60, and 120 minutes post injection. The blood half-life of tPTP was 4.29 minutes. After SPECT/CT imaging (See also FIG. 4) animals (n=5) were sacrificed, organs harvested, and gamma counts assessed. The pancreas showed a 3% injected dose/gram while the metastasis found in the peritoneal cavity showed a 1.5% injected dose/gram, while the highest was in the kidney (see FIG. 6B). The primary route of excretion of $^{111}$IN-tPTP is through the urine.

Binding and Longevity of Tetrameric Peptides Relative to Monomeric Peptides

The tetrameric plectin-1 targeted peptide 4(βAKTLLPTP-GGS(PEG5000))KKKKDOTAβA-NH$_2$ (see chemical structure in FIG. 8) was found to have increased sensitivity over the previously described monomeric peptide (i.e., 600 pmol in tPTP affinity versus 160 nmol affinity with the monomeric peptide). Additionally, because of the addition of β-alanine and PEG, the tetrameric has better longevity and biodistribution than the monomeric peptide because PET reduces toxicity and β-alanine reduces degradation. Furthermore, the labeled tetrameric peptide complex can be visualized quickly (i.e., 1-4 hours) versus a much longer time (i.e., 48 hours) before visualization for the known monomeric peptide.

Amino Acid Substitution of KTLLPTP (SEQ ID NO:1): Alanine Mutation

Figure 9:
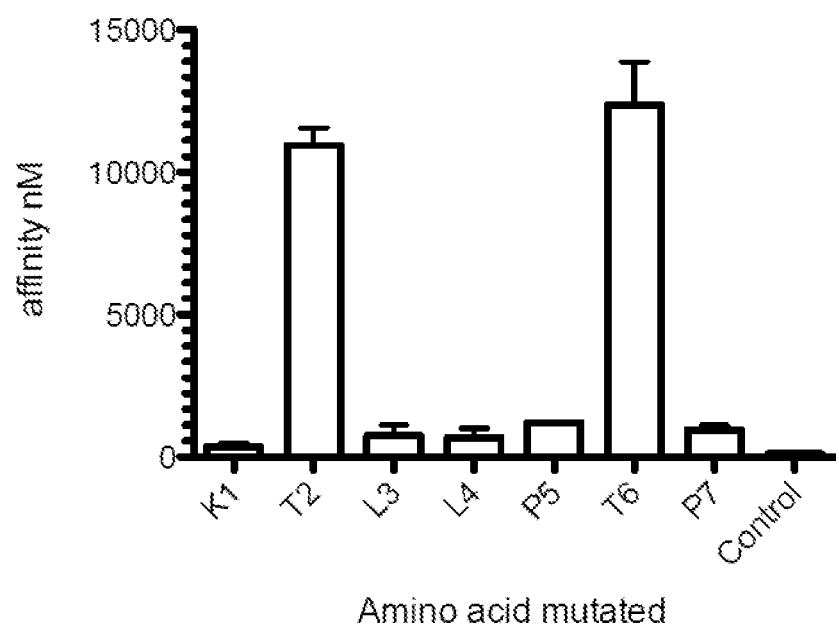
FIG. 9. Amino acid substitution of KTLLPTP (SEQ ID NO:1): Alanine mutations. The peptides used in this study consist of the phage derived sequence KTLLPTP (SEQ ID NO:1; Control), also referred to as Panc 27 peptide and mutated sequences. Each of the seven positions was individually mutated to an alanine. The alanine mutations ATLLPTP, KALLPTP, KTALPTP, KTLAPTP, KTLLATP, KTLLPAP, and KTLLPTA, SEQ ID NOs:9-15 respectively, were made and tested for affinity.

The peptides used in this study consist of the phage derived sequence KTLLPTP (SEQ ID NO:1), also referred to as Panc 27 peptide. Each of the seven positions was individually mutated to an alanine. The alanine mutations ATLLPTP, KALLPTP, KTALPTP, KTLAPTP, KTLLATP, KTLLPAP, and KTLLPTA, SEQ ID NOs:9-15 respectively, were made and tested for affinity. The results are provided in FIG. 9. The data suggest the importance of threonine because substitution of threonine with alanine did reduce affinity, but does not exclude the possibility that adding one or more threonines in any of the other positions of the sequences of the invention would be useful for substitution. The same may be true for proline, but as suggested by the data, to a lesser extent. However, the main criterion for analyzing substitution is whether the resulting substitution has a substantial effect on affinity.

Discussion

Presently, there are no biomarkers available to assist in the detection of early or even preinvasive PDAC. None of the available biomarkers reliably distinguishes PDAC from benign pancreatic disease, most notably chronic pancreatitis. Here, we identify Plec1 as the first novel biomarker that is specifically expressed in early preinvasive, primary and metastatic human PDAC while normal ductal epithelium and ductal epithelial cells in chronic pancreatitis do not express the protein. Furthermore, we show that Plec1 expression may be exploited to detect cancer in the esophagus, stomach, and lung, including metastases. In addition to these findings, we were able to demonstrate in an in-vivo preclinical model that a Plec1 targeting imaging agent can be used for non-invasive imaging of PDAC. This allows the potential incorporation of Plec1 targeted imaging into routine clinical diagnosis and screening measures for PDAC.

Plec1 itself is a typical cytolinker protein of the Plakin family. Plakins connect intermediate filaments to desmosomes and hemidesmosomes, stabilize cells mechanically, regulate cytoskeleton dynamics, and serve as a scaffolding platform for signaling molecules. Furthermore, Plakins are essential for skin and skeletal muscle integrity [18]. Consequently, Plec1 gene mutations were first found in skin disease, such as epidermolysis bullosa [19, 20]. Recently, Plec1 was found to interact with the breast cancer susceptibility gene 2 (BRCA2) [21]. BRCA2 mutations are associated with an increased risk of pancreatic cancer [22, 23]. BRCA2 itself plays an important role in DNA damage repair and is mainly found in the cells nucleus, but has also been identified in the centrosome. The Plec1/BRCA2 interaction plays an important role in the regulation of centrosome localization. Plec1 misexpression therefore leads to displacement of the centrosome and may result in genomic instability and cancer development [21].

PDAC is thought to arise through progression of PanIN I and II lesions to PanIN III (carcinoma in situ) and finally to invasive carcinoma [2, 3, 4]. Based on the data obtained in this study, Plec1 overexpression is acquired during the transition from PanIN I to PanIN II. While only a small fraction of PanIN I (21%) expressed Plec1, half of the PanIN II (54%) and most PanIN III (87%) were Plec1 positive. It thus appears that Plec1 overexpression begins at the stage of PanIN I, even before histological progression to PanIN II and further increases as lesions progress to PDAC. Interestingly, as lesions progress Plec1 not retained at the cell membrane but rather ubiquitously expressed in the cancer cells. Plec1 is only located on the cell membrane in early PanIN I and II lesions, but 27% of the PanIN III and all 31 of the PDAC show membranous and cytoplasmic Plec1 expression. Plec1 expression thus potentially identifies the early PanIN lesions that are destined for progression to cancer. This is of particular importance, since PDAC metastasizes early in its clinical course. Plec1 is therefore the first biomarker for PDAC that is present early in carcinogenesis and whose expression is retained in invasive cancers. This potentially allows for the first time to use a biomarker for the early detection of preinvasive PDAC lesions before they metastasize. Plec1 based screening and diagnosis of PDAC has the potential to overcome many of the shortcomings of currently available diagnostic tools. Unlike CA 19-9, which lacks sensitivity and specificity [5], it is a sensitive and specific biomarker for PDAC. Plec1 based cross-sectional abdominal imaging may in principal be able to reliably detect early stage PDAC, especially in high-risk patients. Additionally, Plec1 overexpression can potentially be exploited to highlight small, currently unidentifiable metastatic foci, thus improving preoperative staging. Furthermore, Plec1 based cross-sectional abdominal imaging should safely differentiate between chronic pancreatitis and PDAC.

Taken together, these data suggest that Plec1 is a sensitive and specific biomarker for primary and metastatic human PDAC as well as early preinvasive cancers. Plec1 targeted imaging can be easily incorporated into diagnostic routine and holds promise of contributing substantially to improving diagnostic accuracy for the detection of PDAC, especially in its early stages before the onset of metastases.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Jemal A, Siegel R, Ward E, Murray T, Xu J, et al. (2007) Cancer statistics, 2007. CA Cancer J Clin 57: 43-66.
2. Hruban R H, Goggins M, Parsons J, Kern S E (2000) Progression model for pancreatic cancer. Clin Cancer Res 6: 2969-2972.
3. Maitra A, Fukushima N, Takaori K, Hruban R H (2005) Precursors to invasive pancreatic cancer. Adv Anat Pathol 12: 81-91.
4. Hruban R H, Takaori K, Klimstra D S, Adsay N V, Albores-Saavedra J, et al. (2004) An illustrated consensus on the classification of pancreatic intraepithelial neoplasia and intraductal papillary mucinous neoplasms. Am J Surg Pathol 28: 977-987.
5. Goggins M (2007) Identifying molecular markers for the early detection of pancreatic neoplasia. Semin Oncol 34: 303-310.

6. Ahmad N A, Kochman M L, Brensinger C, Brugge W R, Faigel D O, et al. (2003) Interobserver agreement among endosonographers for the diagnosis of neoplastic versus non-neoplastic pancreatic cystic lesions. Gastrointest Endosc 58: 59-64.
7. Meining A, Rosch T, Wolf A, Lorenz R, Allescher H D, et al. (2003) High interobserver variability in endosonographic staging of upper gastrointestinal cancers. Z Gastroenterol 41: 391-394.
8. Krishna N B, Mehra M, Reddy A V, Agarwal B (2009) EUS/EUS-FNA for suspected pancreatic cancer: influence of chronic pancreatitis and clinical presentation with or without obstructive jaundice on performance characteristics. Gastrointest Endosc 70: 70-79.
9. Varadarajulu S, Tamhane A, Eloubeidi M A (2005) Yield of EUS-guided FNA of pancreatic masses in the presence or the absence of chronic pancreatitis. Gastrointest Endosc 62: 728-736; quiz 751, 753.
10. Chari S T (2007) Detecting early pancreatic cancer: problems and prospects. Semin Oncol 34: 284-294.
11. Pelaez-Luna M, Takahashi N, Fletcher J G, Chari S T (2007) Resectability of presymptomatic pancreatic cancer and its relationship to onset of diabetes: a retrospective review of CT scans and fasting glucose values prior to diagnosis. Am J Gastroenterol 102: 2157-2163.
12. Fernandez-del Castillo C, Rattner D W, Warshaw A L (1995) Further experience with laparoscopy and peritoneal cytology in the staging of pancreatic cancer. Br J Surg 82: 1127-1129.
13. John T G, Greig J D, Carter D C, Garden O J (1995) Carcinoma of the pancreatic head and periampullary region. Tumor staging with laparoscopy and laparoscopic ultrasonography. Ann Surg 221: 156-164.
14. Boll D T, Merkle E M (2003) Differentiating a chronic hyperplastic mass from pancreatic cancer: a challenge remaining in multidetector CT of the pancreas. Eur Radiol 13 Suppl 5: M42-49.
15. Oto A, Eltorky M A, Dave A, Ernst R D, Chen K, et al. (2006) Mimics of pancreatic malignancy in patients with chronic pancreatitis: correlation of computed tomography imaging features with histopathologic findings. Curr Probl Diagn Radiol 35: 199-205.
16. Furukawa H, Okada S, Saisho H, Ariyama J, Karasawa E, et al. (1996) Clinicopathologic features of small pancreatic adenocarcinoma. A collective study. Cancer 78: 986-990.
17. Kelly K A, Bardeesy N, Anbazhagan R, Gurumurthy S, Berger J, et al. (2008) Targeted nanoparticles for imaging incipient pancreatic ductal adenocarcinoma. PLoS Med 5: e85.
18. Sonnenberg A, Liem R K (2007) Plakins in development and disease. Exp Cell Res 313: 2189-2203.
19. Pfendner E, Uitto J (2005) Plectin gene mutations can cause epidermolysis bullosa with pyloric atresia. J Invest Dermatol 124: 111-115.
20. Pulkkinen L, Smith F J, Shimizu H, Murata S, Yaoita H, et al. (1996) Homozygous deletion mutations in the plectin gene (PLEC1) in patients with epidermolysis bullosa simplex associated with late-onset muscular dystrophy. Hum Mol Genet 5: 1539-1546.
21. Niwa T, Saito H, Imajoh-Ohmi S, Kaminishi M, Seto Y, et al. (2009) BRCA2 interacts with the cytoskeletal linker protein plectin to form a complex controlling centrosome localization. Cancer Sci.
22. Bausch et al., 2009, J. Gastrointest. Surg., 13:1948.
23. Harris, 2009, J. Clin. Oncology, 27, No. 15S (May 20 Supplement): e22118.
24. Lee, 2004, J. Med., 35:(1-6):141-149.
25. International Patent Application Publication No. WO 2009/129220, Kelly, et al., published Oct. 22, 2009.
26. Karlin and Altschul (1990, Proc. Natl. Acad. Sci. USA 87:2264-2268.
27. Karlin and Altschul (1993, Proc. Natl. Acad. Sci. USA 90:5873-5877.
28. Altschul, et al. (1990, J. Mol. Biol. 215:403-410.
29. Altschul et al. (1997, Nucleic Acids Res. 25:3389-3402.
30. Gross and Mienhofer, eds., *The Peptides*, vol. 3, pp. 3-88 (Academic Press, New York, 1981.
31. Gerhardt et al., eds., 1994, *Methods for General and Molecular Bacteriology*, American Society for Microbiology, Washington, D.C., p. 574.
32. Devereux et al., 1984 Nucl. Acids Res. 12:387.
33. Altschul et al., 1990 Proc. Natl. Acad. Sci. USA. 1990 87:14:5509-13.
34. Altschul et al., J. Mol. Biol. 1990 215:3:403-10; Altschul et al., 1997 Nucleic Acids Res. 25:3389-3402.
35. Li, 2007, J. Nuc. Med., 48:7:1162-1171, "$^{64}$Cu-labeled tetrameric and octameric RGD peptides for small-animal PET of tumor $\alpha_v\beta_3$ integrin expression".
36. Reviewed in Choe and Lee, 2007, Current Pharmaceutical Design, 13:17-31.
37. Chen et al., 2004, Mol. Imaging Biol. 6:350-9, "MicroPET imaging of breast cancer alpha$_v$-integrin expression with $^{64}$Cu-labeled dimeric RGD peptides".
38. Janssen, 2002, Cancer Biother. Radiophamr., 17:641-6, "Comparison of monomeric and dimeric radiolabeled RGD-peptide for tumor targeting.
39. Poethko, 2004, J. Nucl. Med. 45:892-902.
40. Chen, 2004, Bioconjugate Chem., 15:41-9.
41. Chen, 2004, Nucl. Med. Biol., 31:11-19, "Pharmacokinetics and tumor retention of $^{125}$I-labeled RGD peptide are improved by PEGylation".
42. Li et al., 2009, Mol. Cancer Ther., 8:5:1239-1249.
43. U.S. Pat. No. 7,666,979 (issued from U.S. patent application Ser. No. 10/661,032), Fan, et al., "Methods for Preparing Multivalent Constructs for Therapeutic and Diagnostic Applications and Methods of Preparing the Same, Feb. 23, 2010.
44. U.S. patent application Ser. No. 12/012,011 (continuation of U.S. patent application Ser. No. 10/792,582).
45. Nahrendorf, 2010, JACC: Cardiovascular Imaging, 2:10: 1213-1222.
46. Krajewski et al., 2005, "Effect of Dimerization and Tetramerization on the Potency of HIV-Integrase Inhibitory Peptides," in Understanding Biology Using Peptides, American Peptide Society, S. Blondelle, Editor, 411-412).
47. Yim et al., 2010, J. Med. Chem., 53:3944-3953.
48. Dijkgraaf et al., 2010, Eur. J. Nucl. Med. Mol. Imaging, published online 21 Sep. 2010.
49. U.S. patent application Ser. No. 10/792,582; Dransfield et al., U.S. Pat. Pub. Nos. US 2010/0261875; U.S. Pat. No. 7,666,979).
50. See Sosabowski et al., Nature Protocols 1, —972-976 (2006) and Leon-Rodriguez et al., Bioconjugate chemistry, Jan. 3, 2008; 19(2):391-402).
51. U.S. patent application Ser. No. 12/112,289
52. Kyte & Doolittle, 1982, J. Mol. Biol., 157:105-132.
53. Chou & Fasman, 1974, Biochemistry, 13:222-245;
54. 1978, Ann. Rev. Biochem., 47: 251-276; 1979, Biophys. J., 26:367-384).
55. PROWL Rockefeller University website
56. Stewart et al. in *Solid Phase Peptide Synthesis,* 2nd Edition, 1984, Pierce Chemical Company, Rockford, Ill.
57. Bodanszky and Bodanszky in *The Practice of Peptide Synthesis,* 1984, Springer-Verlag, New York.

58. Deutscher et al. (ed., 1990, *Guide to Protein Purification*, Harcourt Brace Jovanovich, San Diego).
60. Gait, 1985, OLIGONUCLEOTIDE SYNTHESIS: A PRACTICAL APPROACH (IRL Press, Oxford, England.
61. Kohler and Milstein (1975, *Nature* 256:495-497.
62. Kozbor et al., 1983, *Immunology Today* 4:72).
63. Cole et al., 1985, in *Monoclonal Antibodies and Cancer Therapy*, Alan R. Liss, Inc., pp. 77-96.
64. Cote et al., 1983, *Proc. Natl. Acad. Sci. U.S.A.* 80:2026-2030.
65. Morrison et al., 1984, *Proc. Natl. Acad. Sci. U.S.A.* 81:6851-6855;
66. Neuberger et al., 1984, *Nature* 312:604-608;
67. Takeda et al., 1985, *Nature* 314:452-454.
68. U.S. Pat. No. 4,946,778
69. Huse et al., 1989, *Science* 246:1275-1281.
70. Harlow et al. (1988, In: Antibodies, A Laboratory Manual, Cold Spring Harbor, N.Y.
71. Tuszynski et al. (1988, Blood, 72:109-115).
72. Wright et al. (1992, Critical Rev. in Immunol. 12(3,4): 125-168.
73. Gu et al. (1997, Thrombosis and Hematocyst 77(4):755-759.
74. Sambrook et al. (1989, Molecular Cloning: A Laboratory Manual, Cold Spring Harbor, N.Y.).
75. Burton et al., 1994, Adv. Immunol. 57:191-280.
76. Marks et al., 1991, J. Mol. Biol. 222:581-597.
77. Barbas, 1995, Nature Medicine 1:837-839; de Kruif et al. 1995, J. Mol. Biol. 248:97-105.
78. Klug et al., Mol. Biol. Reports 20:97-107 (1994).
79. Wallis et al., Chem. Biol. 2:543-552 (1995).
80. Ellington, Curr. Biol. 4:427-429 (1994); Lato et al., Chem. Biol. 2:291-303 (1995).
81. Conrad et al., Mol. Div. 1:69-78 (1995).
82. Uphoff et al., Curr. Opin. Struct. Biol. 6:281-287 (1996).
83. Fields and Song, Nature (London), 340:245-246 (1989).
84. Chien et al., Proc. Natl. Acad. Sci. USA, 88:9578-9582 (1991).
85. Chevray and Nathans, Proc. Natl. Acad. Sci. USA, 89: 5789-5793 (1991).
86. Watt, 2006, Nature Biotechnology, 24:177;
87. Watt, U.S. Pat. No. 6,994,982;
88. Watt, U.S. Pat. Pub. No. 2005/0287580;
89. Watt, U.S. Pat. No. 6,510,495
90. U.S. Pat. No. 5,789,543
91. U.S. Pat. No. 6,207,718
92. Remington's Pharmaceutical Science (15th ed., Mack Publishing, Easton, Pa., 1980).
93. Genaro, ed., 1985, *Remington's Pharmaceutical Sciences*, Mack Publishing Co., Easton, Pa.
94. Burrows, et al., "Peptide-MHC Class I Tetrameric Complexes Display Exquisite Ligand Specificity", J of Immunology, 2000; 6229-6234.
95. Chakraborty, et al., "Evaluation of $^{111}$In-Labeled Cyclic RGD Peptides: Tetrameric not Tetravalent", Biconjugate Chem., 2010, 21, 969-978.
96. Ponticelli, et al., "Modulation of Angiogenesis by a Tetrameric Tripeptide That Antagonizes Vascular Endothelial Growth Factor Receptor 1", J of Biological Chemistry, 2008, Vol. 283, No. 49, 34250-34259.
97. Choe, et al., "Targeted In Vivo of Angiogenesis: Present Status and Perspectives", Current Pharmaceutical Design, 2007, 13, 17-31.
98. Chang, et al., "Tetrameric Cytokines with Improved Biological Activity", Jul. 29, 2010.

What is claimed is:

1. A tetrameric peptide ligand complex for binding to Plectin-1 or a homolog or fragment thereof, wherein said complex has the formula $(\beta AKTLLPTPGGS(PEG5000))_4$ KKKKDOTA$\beta$A-NH$_2$, wherein said tetrameric complex has a Ki of about $8.3 \times 10^{-7}$ M.

2. A method for detecting Plectin-1 or a homolog or fragment thereof in a subject, comprising administering to a subject a tetrameric peptide ligand complex of claim 1 further comprising an imaging agent, and detecting the location of cells comprising Plectin-1 by detecting said imagining agent.

3. The method of claim 2, wherein said imaging agent is $^{111}$In.

4. The method of claim 2, wherein said imaging agent is detected by using a single photon emission computed tomography (SPECT/CT) scanner coupled to a computer, and analyzing imaging data using a program.

5. The method of claim 2, wherein said imaging agent is selected from the group consisting of a radionuclide, a radiological contrast agent, a paramagnetic ion, a metal, a biological tag, a fluorescent label, a chemiluminescent label, an ultrasound contrast agent and a photoactive agent.

6. The method of claim 2, wherein said Plectin-1 or a homolog or fragment thereof is a cell surface Plectin-1 or a homolog or fragment thereof.

7. A pharmaceutical composition comprising a pharmaceutically-acceptable carrier and the tetrameric peptide ligand complex of claim 1.

8. A kit comprising a pharmaceutical composition comprising a pharmaceutically-acceptable carrier and the tetrameric peptide ligand complex of claim 1, an applicator, and a instructional material for the use thereof, and optionally an imaging agent and a therapeutic agent.

9. A tetrameric peptide ligand complex for detecting Plectin-1 or a homolog or fragment thereof in a subject comprising an imaging agent, wherein said complex has the structure:

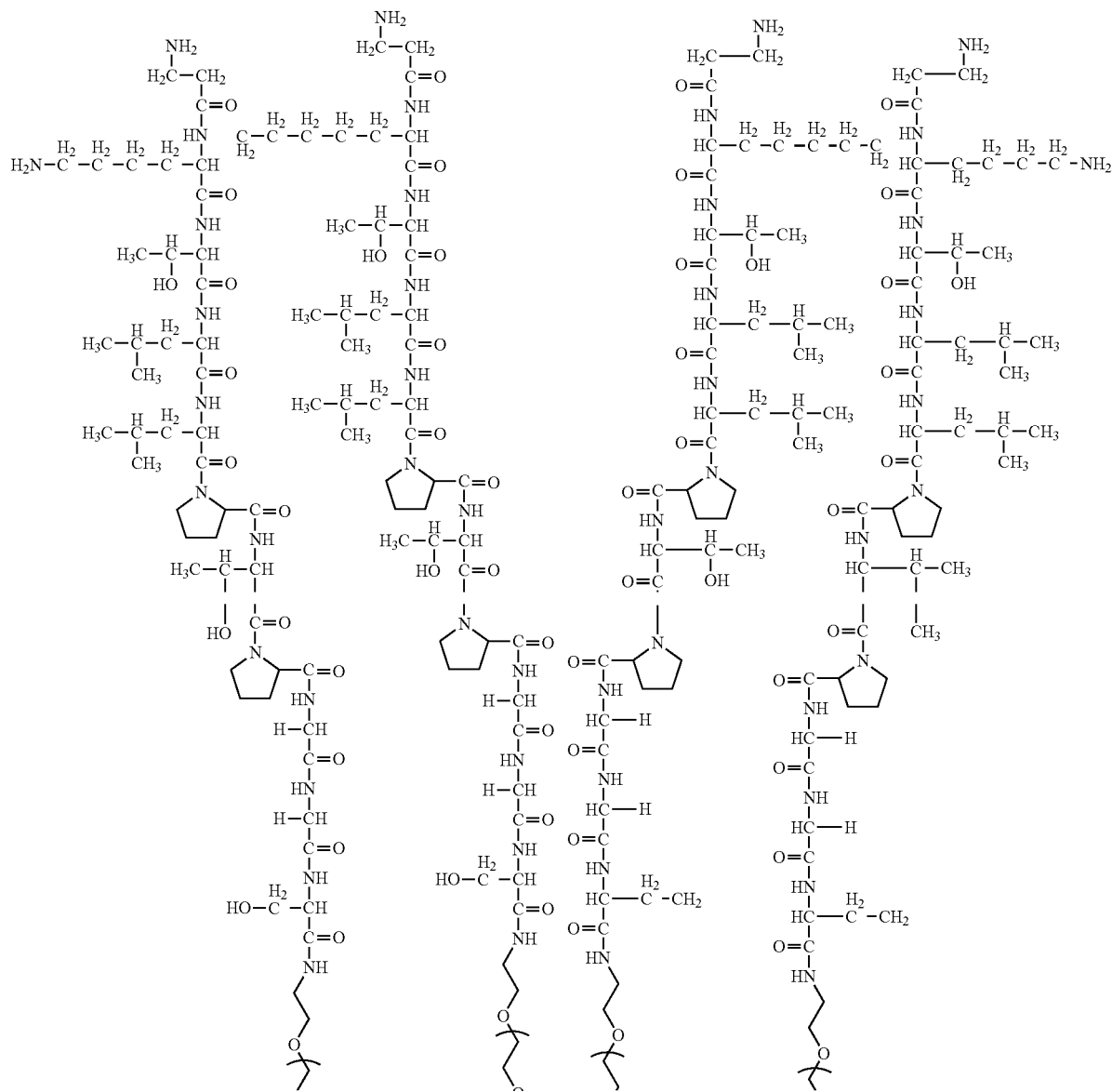

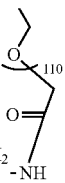
-continued

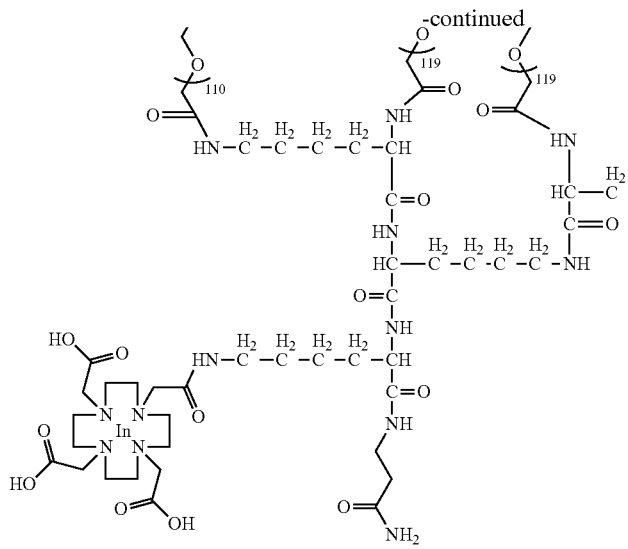

wherein said tetrameric complex has a Ki of about $8.3 \times 10^{-7}$ M.

10. A tetrameric peptide ligand complex for binding to Plectin-1 or a homolog or fragment thereof, wherein said complex has the formula $(\beta AKTLLPTPGGS(PEG5000))_4 KKKKX\beta A\text{-}NH_2$, wherein X is a chelating agent.

11. The tetrameric peptide ligand complex of claim 10, wherein said chelating agent is selected from the group consisting of DTPA, DO3A, DOTA, EDTA, TETA, EHPG, HBED, NOTA, DOTMA, TETMA, PDTA, TTHA, LICAM, HYNIC, MECAM, and deferoxamine.

12. The tetrameric peptide ligand complex of claim 10, wherein said chelating agent is DOTA.

13. The tetrameric peptide ligand complex of claim 10, further comprising an imaging agent coupled to the chelating agent, wherein the imaging agent is selected from the group consisting of a radionuclide, a radiological contrast agent, a paramagnetic ion, a metal, a biological tag, a fluorescent label, a chemiluminescent label, an ultrasound contrast agent and a photoactive agent.

14. The tetrameric peptide ligand complex of claim 13, wherein the imaging agent is a radionuclide.

15. The tetrameric peptide ligand complex of claim 14, wherein the radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154\text{-}158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, and other gamma-, beta-, or positron-emitters.

16. The tetrameric peptide ligand complex of claim 10, wherein the chelating agent is coupled to a radionuclide.

17. The tetrameric peptide ligand complex of claim 16, wherein said radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154\text{-}158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, and other gamma-, beta-, or positron-emitters.

18. The tetrameric peptide ligand complex of claim 16, wherein the radionuclide is $^{111}$In.

19. The tetrameric peptide ligand of claim 12, wherein said complex has the structure:

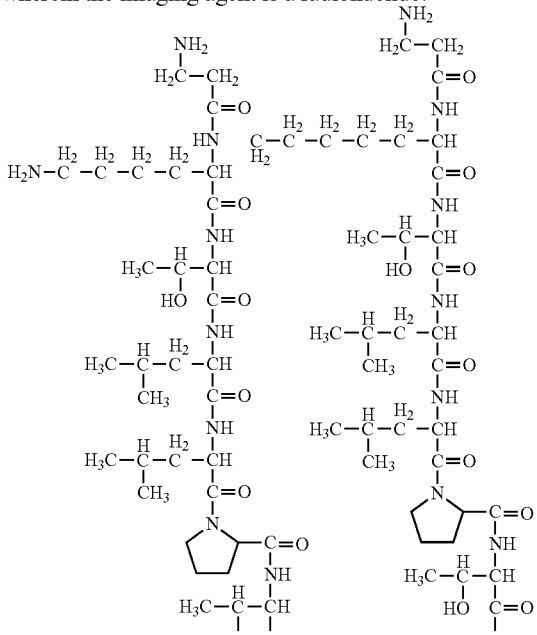
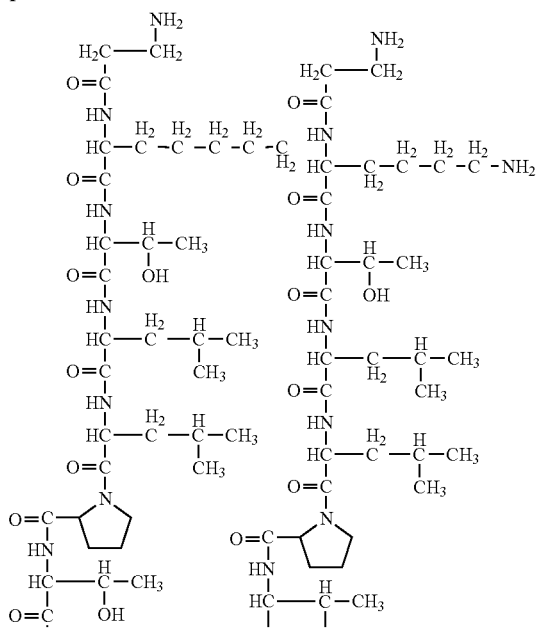

77
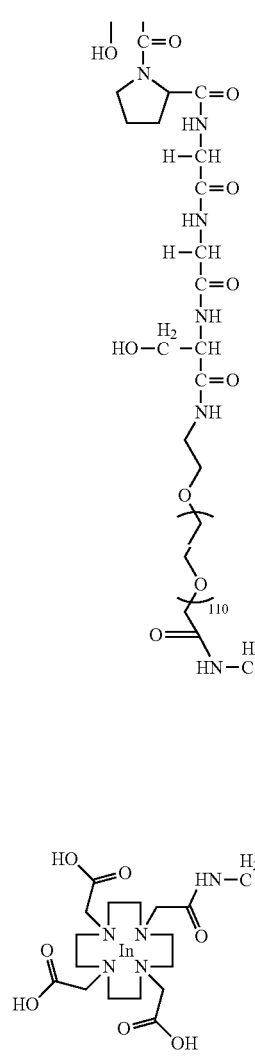
-continued
78
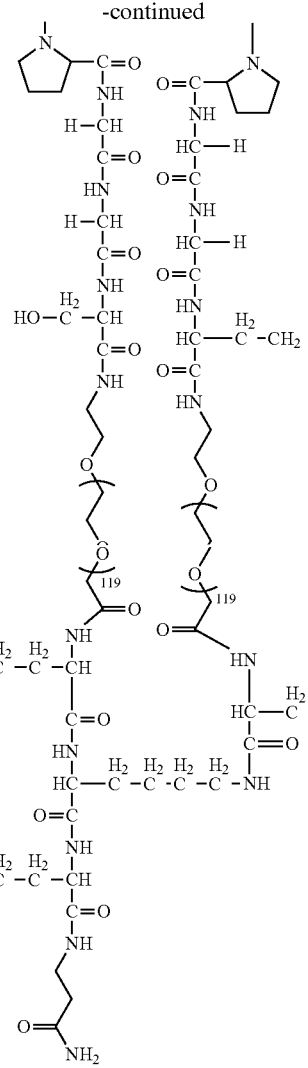
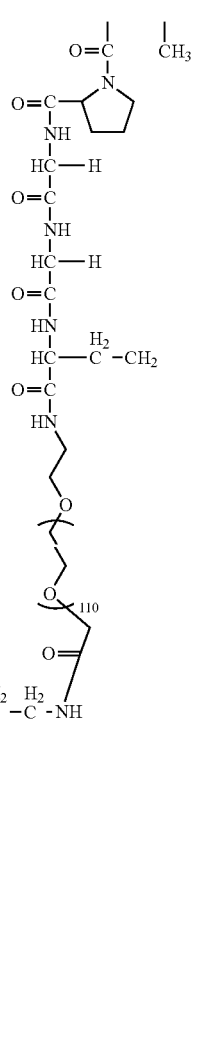
* * * * *

UNITED STATES PATENT AND TRADEMARK OFFICE
CERTIFICATE OF CORRECTION

PATENT NO.      : 9,075,059 B2
APPLICATION NO. : 13/508120
DATED           : July 7, 2015
INVENTOR(S)     : Kelly Page 1 of 1

It is certified that error appears in the above-identified patent and that said Letters Patent is hereby corrected as shown below:

In the specification

Column 1, line 15-18, delete "United States Government support under Grant Nos. NIH-P50-CA86355 and P01-CA117969-01, awarded by The National Institutes of Health. The United States Government" and insert --government support under CA137071, CA086355, CA117969 awarded by the National Institutes of Health. The government--, therefor Signed and Sealed this
Sixteenth Day of August, 2016

Michelle K. Lee
*Director of the United States Patent and Trademark Office*